(12) United States Patent
Flitsch

(10) Patent No.: US 11,302,516 B2
(45) Date of Patent: Apr. 12, 2022

(54) METHOD AND APPARATUS FOR AN IMAGING SYSTEM

(71) Applicant: Frederick A. Flitsch, New Windsor, NY (US)

(72) Inventor: Frederick A. Flitsch, New Windsor, NY (US)

( * ) Notice: Subject to any disclaimer, the term of this patent is extended or adjusted under 35 U.S.C. 154(b) by 125 days.

(21) Appl. No.: 16/805,005

(22) Filed: Feb. 28, 2020

(65) Prior Publication Data

US 2020/0203123 A1 Jun. 25, 2020

Related U.S. Application Data

(63) Continuation-in-part of application No. 16/036,663, filed on Jul. 16, 2018, which is a continuation-in-part of application No. 15/595,759, filed on May 15, 2017, now Pat. No. 10,049,853, which is a continuation-in-part of application No. 15/380,649, filed on Dec. 15, 2016, now Pat. No. 9,697,986, which is a continuation-in-part of application No. 14/861,737, filed on Sep. 22, 2015, now Pat. No. 9,558,915, which is a continuation-in-part of application No. 14/594,335, filed on Jan. 12, 2015, now Pat. No. 9,171,697.

(60) Provisional application No. 61/926,471, filed on Jan. 13, 2014.

(51) Int. Cl.
*B01L 3/02* (2006.01)
*C12Q 1/02* (2006.01)
*H01J 37/317* (2006.01)
*H01L 41/053* (2006.01)
*B33Y 30/00* (2015.01)

(52) U.S. Cl.
CPC .......... *H01J 37/317* (2013.01); *B01L 3/0268* (2013.01); *B33Y 30/00* (2014.12); *C12Q 1/02* (2013.01); *H01L 41/053* (2013.01)

(58) Field of Classification Search
CPC ......... B01L 3/0268; B33Y 30/00; C12Q 1/02; H01J 37/252; H01J 37/317; H01J 2237/2583; H01L 41/053; H02N 2/02; G01N 33/54366
See application file for complete search history.

(56) References Cited

U.S. PATENT DOCUMENTS

| | | |
|---|---|---|
| 5,784,166 A | 7/1998 | Sogard |
| 5,959,354 A * | 9/1999 | Smith ................ H01L 23/544 257/734 |
| 6,897,941 B2 | 5/2005 | Almogy |
| 7,193,722 B2 | 3/2007 | Boogaarts et al. |
| 7,513,822 B2 | 4/2009 | Flitsch |
| 7,733,364 B2 | 6/2010 | Nomura et al. |
| 7,777,202 B2 | 8/2010 | Satoh et al. |
| 8,229,585 B2 | 7/2012 | Flitsch |
| 8,300,076 B2 | 10/2012 | Nomura et al. |
| 8,384,048 B2 | 2/2013 | Wiesner |
| 8,982,275 B2 | 3/2015 | Suenobu |
| 9,059,227 B2 | 6/2015 | Flitsch |
| 9,171,697 B2 | 10/2015 | Flitsch |

(Continued)

*Primary Examiner* — Anh T Vo

(57) ABSTRACT

The present invention provides apparatus for an imaging system comprising a multitude of chemical emitting elements upon a substrate. In some embodiments the substrate may be approximately round with a radius of approximately one inch. Various methods relating to using and producing an imaging system of chemical emitters are disclosed.

5 Claims, 25 Drawing Sheets

(56) References Cited

U.S. PATENT DOCUMENTS

| | | |
|---|---|---|
| 9,558,915 B2 | 1/2017 | Flitsch |
| 2010/0231812 A1 | 9/2010 | Hall |
| 2012/0106151 A1 | 5/2012 | Marie et al. |
| 2019/0156919 A1 | 5/2019 | Magis et al. |

\* cited by examiner

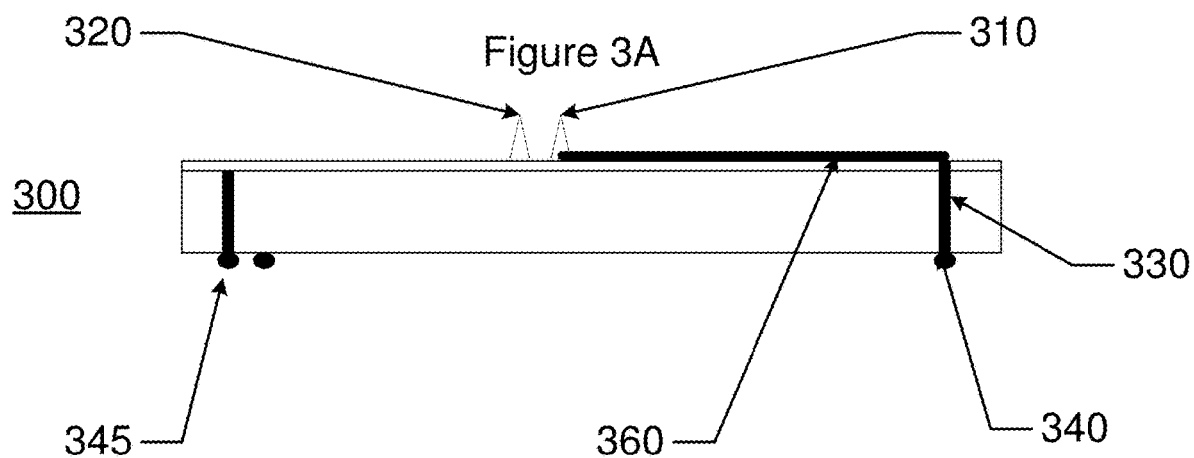
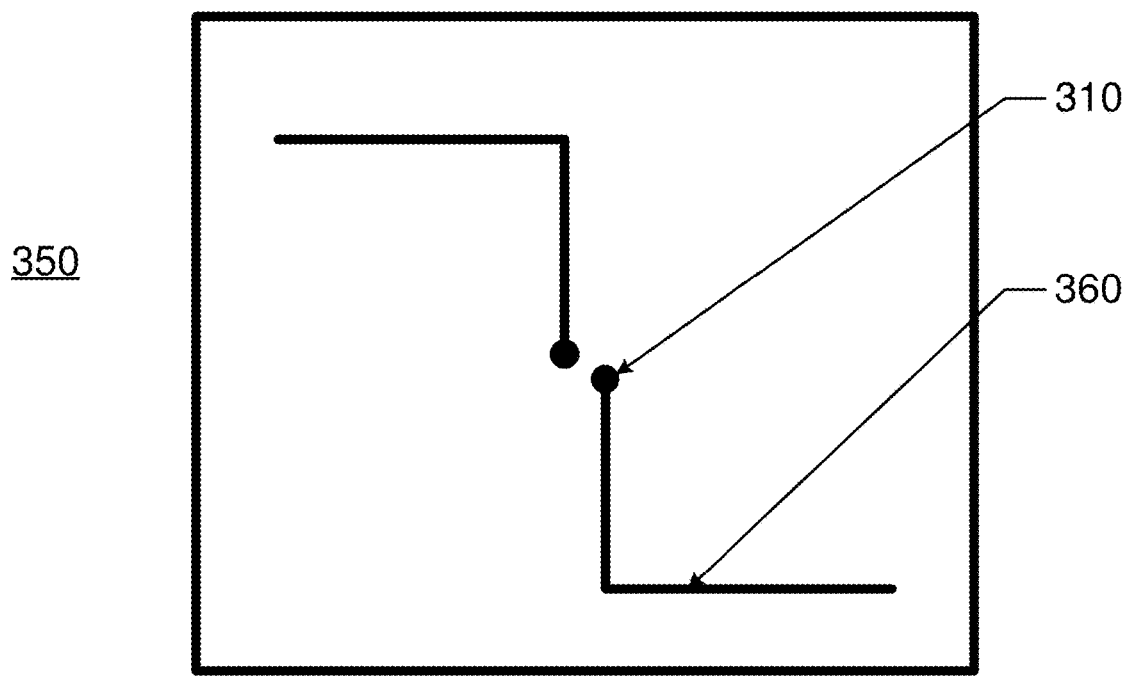

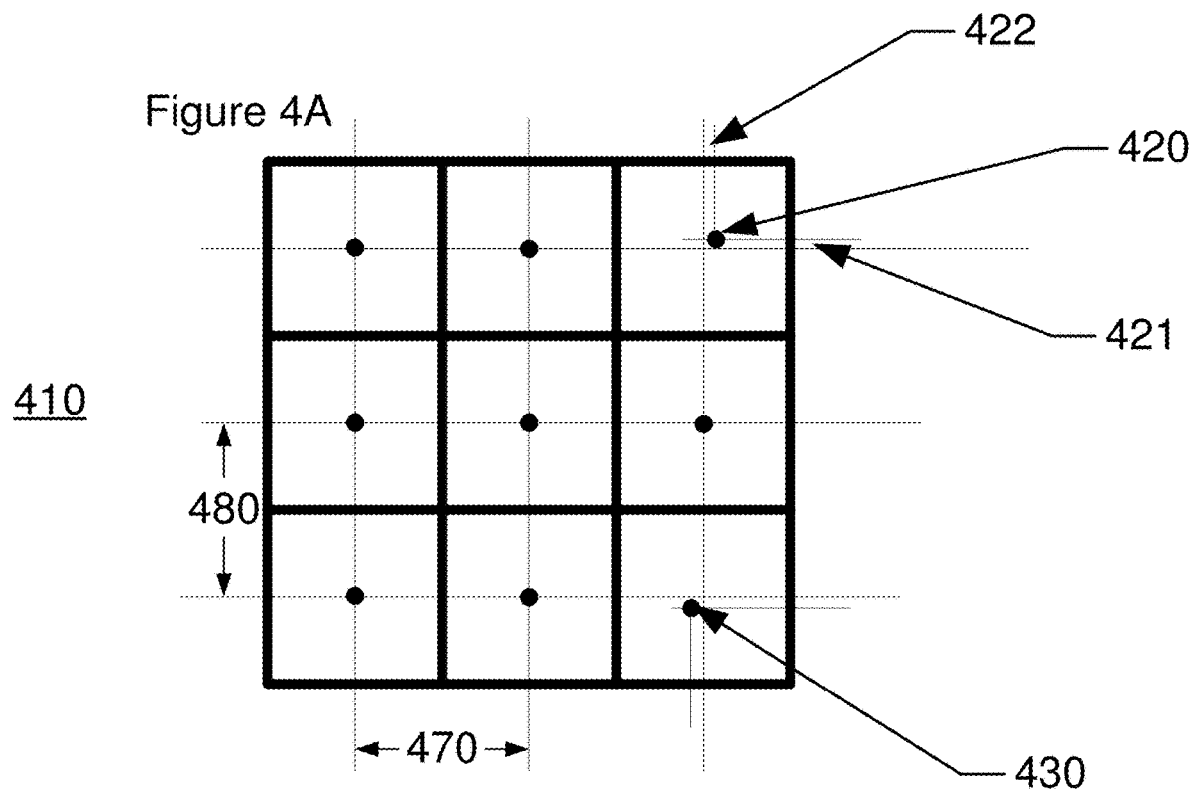
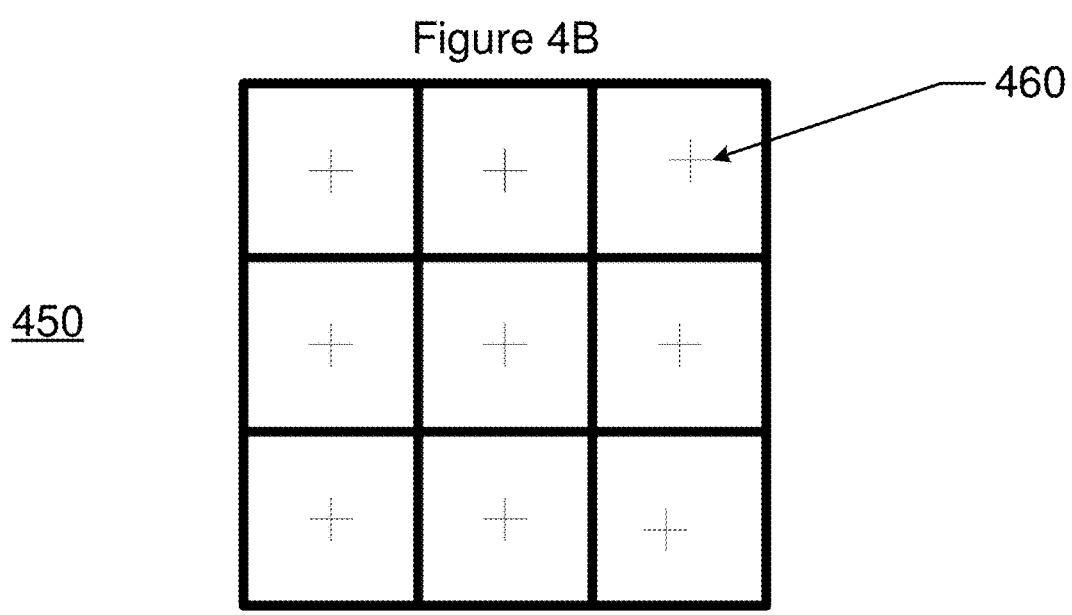

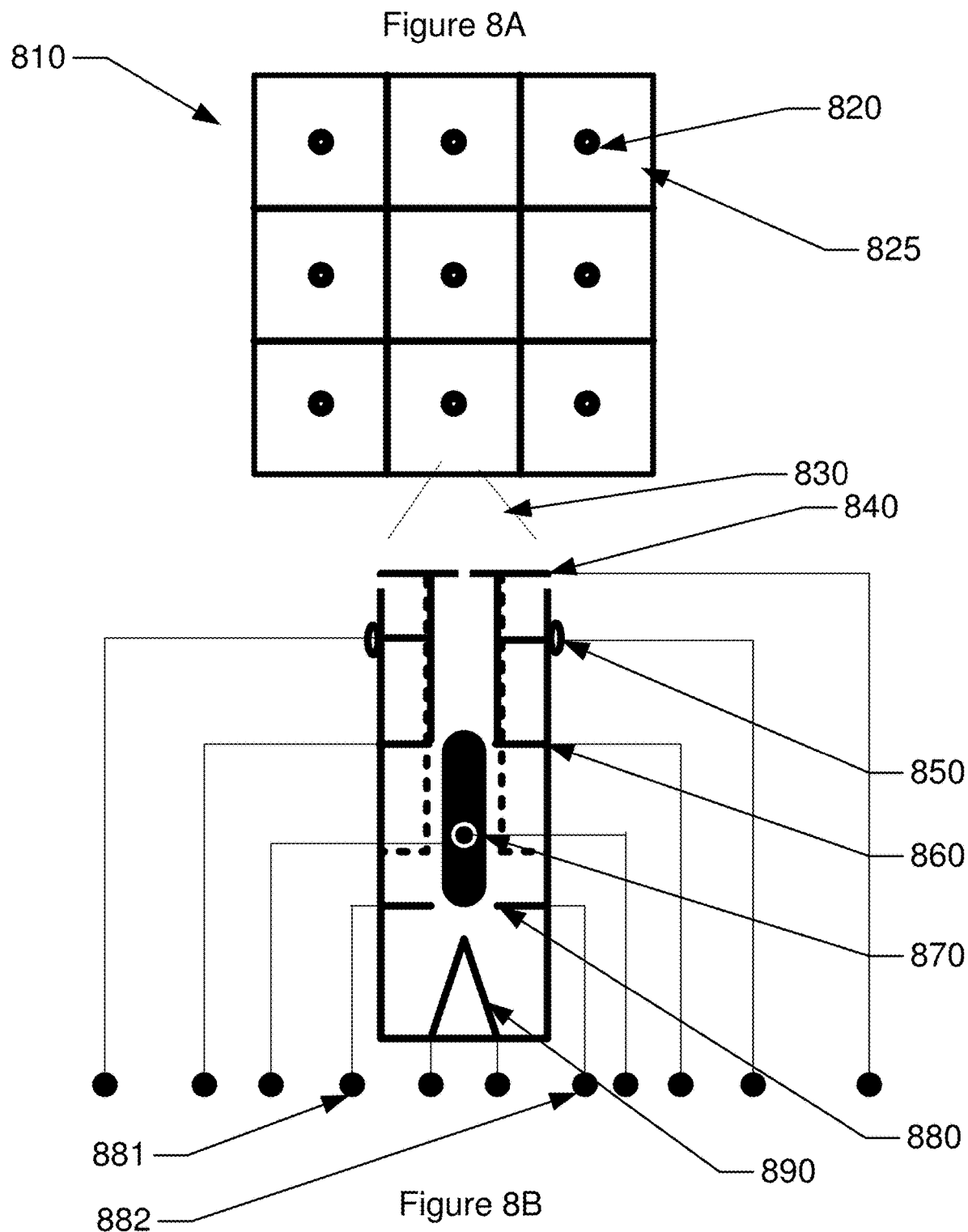

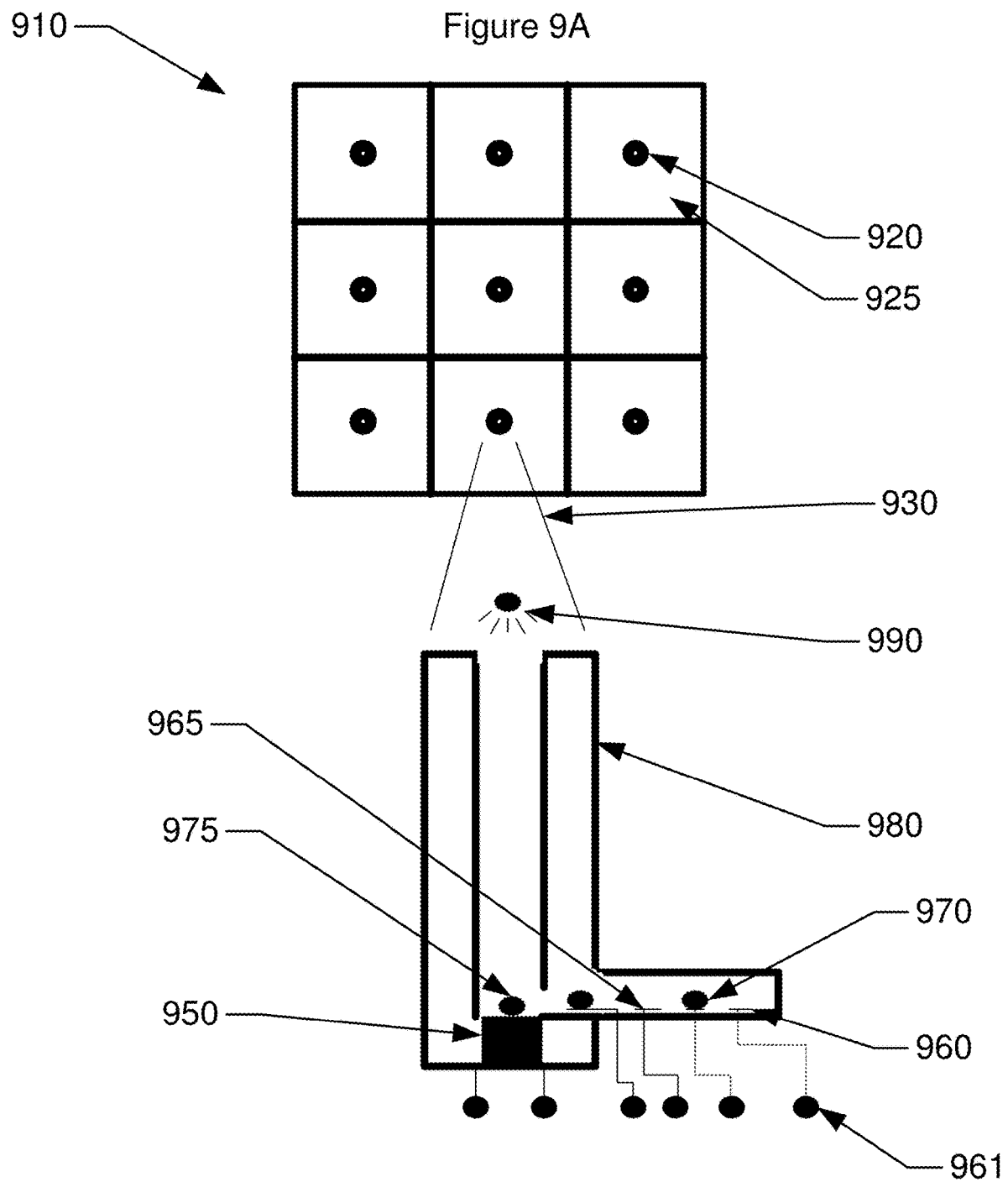

METHOD AND APPARATUS FOR AN IMAGING SYSTEM

CROSS REFERENCE TO RELATED APPLICATIONS

This application is a continuation in part of the Utility application Ser. No. 16/036,663, filed Jul. 16, 2018 and entitled: "METHOD AND APPARATUS FOR AN IMAGING SYSTEM", which in turn is a continuation in part of the Utility application Ser. No. 15/595,759, filed May 15, 2017 and entitled: "METHOD AND APPARATUS FOR AN IMAGING SYSTEM OF BIOLOGICAL MATERIAL," which in turn is a continuation in part of the Utility application Ser. No. 15/380,649, filed Dec. 15, 2016 and entitled: "METHOD AND APPARATUS FOR AN ELECTROMAGNETIC EMISSION BASED IMAGING SYSTEM." The application Ser. No. 14/861,737 in turn is a continuation in part of the Utility application Ser. No. 14/861,737, filed Sep. 22, 2015 and entitled: "METHOD AND APPARATUS FOR A HIGH RESOLUTION IMAGING SYSTEM." The application Ser. No. 14/861,737 in turn is a continuation in part of the Utility application Ser. No. 14/594,335, filed Jan. 12, 2015 and entitled: "METHOD AND APPARATUS FOR AN IMAGING SYSTEM." The application Ser. No. 14/594,335 in turn claims the benefit of the U.S. Provisional Application Ser. No. 61/926,471, filed Jan. 13, 2014 and entitled METHOD AND APPARATUS FOR AN IMAGING SYSTEM. The contents of each are relied upon and hereby incorporated by reference.

FIELD OF THE INVENTION

The present invention relates to methods and associated apparatus and methods which relate to processing tools used to create imaged layers on substrates. Massively parallel implements of electron beam or chemical species beam imaging elements may be combined to form a full substrate processing system. In some embodiments the imaging systems may be used in conjunction with cleanspace fabricators. The present invention may also relate to methods and apparatus to capitalize on the advantages of cleanspace fabricators for methods or development, design, research and manufacturing.

BACKGROUND OF THE INVENTION

A known approach to advanced technology fabrication of materials such as semi-conductor substrates is to assemble a manufacturing facility as a "cleanroom." In such cleanrooms, processing tools are arranged to provide aisle space for human operators or automation equipment. Exemplary cleanroom design is described in: "Cleanroom Design, Second Edition," edited by W. Whyte, published by John Wiley & Sons, 1999, ISBN 0-471-94204-9, (herein after referred to as "the Whyte text" and the content of which is included for reference in its entirety).

Cleanroom design has evolved over time to include locating processing stations within clean hoods. Vertical unidirectional airflow can be directed through a raised floor, with separate cores for the tools and aisles. It is also known to have specialized mini-environments which surround only a processing tool for added space cleanliness. Another known approach includes the "ballroom" approach, wherein tools, operators and automation all reside in the same cleanroom.

Evolutionary improvements have enabled higher yields and the production of devices with smaller geometries. However, known cleanroom design has disadvantages and limitations.

For example, as the size of tools has increased and the dimensions of cleanrooms have increased, the volume of cleanspace that is controlled has concomitantly increased. As a result, the cost of building the cleanspace, and the cost of maintaining the cleanliness of such cleanspace, has increased considerably.

Tool installation in a cleanroom can be difficult. The initial "fit up" of a "fab" with tools, when the floor space is relatively empty, can be relatively straightforward. However, as tools are put in place and a fabricator begins to process substrates, it can become increasingly difficult and disruptive of job flow, to either place new tools or remove old ones. Likewise it has been difficult to remove a subassembly or component that makes up a fabricator tool in order to perform maintenance or replace such a subassembly or component of the fabricator tool. It would be desirable therefore to reduce installation difficulties attendant to dense tool placement while still maintaining such density, since denser tool placement otherwise affords substantial economic advantages relating to cleanroom construction and maintenance.

There are many types of manufacturing flows and varied types of substrates that may be operated effectively in the mentioned novel cleanspace environments. It would be desirable to define standard methodology of design and use of standard componentry strategies that would be useful for manufacturing flows of various different types; especially where such flows are currently operated in non-cleanroom environments.

In many types of substrate processing environments, a common and important processing step may include "lithography" processing where images are imparted to films of sensitive material upon the substrate. In the state of the art optical lithography is used to impart images through lithography masks. In other embodiments, electron beams are used to impart images in a controllable fashion. There may be utility for creating systems where imaging systems may be formed with large parallel combinations of imaging elements that process a full substrate simultaneously. Such imaging elements that process a full substrate simultaneously may also be consistent with the desire to reduce installation difficulties for processing tools as previously mentioned.

SUMMARY OF THE INVENTION

Accordingly, the present invention provides apparatus and methods to provide parallel implementations of electron beam or chemical species beam imaging elements to form a full substrate processing system. In some embodiments these systems may be used within a cleanspace fabricator facility. Cleanspace fabrication facilities have been defined in various patent specifications by the inventive entity, and the teachings and definition of these published specification may form a basis for understanding the utility of the inventive art herein within cleanspace environments.

The present invention also provides novel methods of utilizing these designs for processing fabs which rearrange the clean room into a cleanspace and thereby allow processing tools to reside in both vertical and horizontal dimensions relative to each other and in some embodiments with their tool bodies outside of, or on the periphery of, a clean space of the fabricator. In such a design, the tool bodies can be removed and replaced with much greater ease than is the standard case. The design also anticipates the automated transfer of substrates inside a clean space from a tool port of one tool to another. The substrates can reside inside specialized carriers designed to carry ones substrate at a time. Further design enhancements can entail the use of automated equipment to carry and support the tool body movement into and out of the fab environment. In this invention, numerous methods of using some or all of these innovations in designing, operating or otherwise interacting with such fabricator environments are described. The present invention can therefore include methods and apparatus for situating processing tools in a vertical dimension and control software modules for making such tools functional both within the cleanspace entity itself and also in networks of such fabricators wherein at least one of the processing tools incorporates an imaging system comprised of a multitude of imaging elements.

In some embodiments of the invention, methods are provided which utilize at least one fabricator where the cleanspace is vertically deployed. Within said fabricator there will be at least one and typically more tool chassis and toolPods. A toolPod will typically be attached to a tool chassis directly or indirectly thorough one or more other piece or pieces of equipment which attach to the toolPod. At least the one fabricator will perform a process in one of the toolPods and typically will perform a process flow which will be performed in at least one toolPod. The toolPod may have an attached or integral Toolport that is useful for the transport of substrates from one tool or toolPod to another tool or toolPod. In these embodiments, a unique aspect of the embodiments is that the first toolPod may be removed from the fabricator or factory for a maintenance activity or repair and then replaced with another toolPod. The use of the tool chassis together with a toolPod may result in a replacement that takes less than a day to perform. In some cases the replacement may take less than an hour. There may be numerous reasons for the replacement. It may be to repair the first toolPod or it may be replace the toolPod with another toolPod where the tool within is of a different or newer design type. These methods may be additionally useful to product a product when the substrate produced by the process flow may next be processed with additional steps including those which dice or cut or segment the substrate into subsections which may be called chips. The chips may then be assembled into packages to form a product. The assembly and packaging steps may also comprise a process flow and may include sophisticated techniques including three dimensional assembly, through silicon vias, substrate stacking to mention a few; and these steps may be performed in a cleanspace fabricator or alternatively in a cleanroom type fabricator. The assembly and packaging operations may include steps for thinning substrates as well as steps to form conductive connections between conductive contacts or contacts and other conductive surfaces. Alternatively, the end product of the assembly and packaging operations which may be an assembled product may be used in method where a conductive connection is formed between a conductive contact of the package and another conductive surface of another component or entity. Any of the major types of processing may utilize an imaging apparatus comprised of a multitude of imaging elements.

In some embodiments, the methods of producing products in the mentioned cleanspace fabricator may be useful to produce small amounts of a product. An imaging system comprised of a multitude of individual imaging elements may define a lithography option for a low volume fabricator that is both economical and cost effective in that expenses such as the production of lithography masks may not be required in some embodiments. In some cases the fabricator environment may be useful in creating and producing imaging system components as well.

There may be combinations of toolPods and tool Chassis entities which reside in environments that resemble either cleanspace or cleanroom environments which represent novel methods based on the inventive art herein. These collections may also create methods for the use of imaging systems comprise of a multitude of individual imaging elements. For example, a vertically deployed cleanspace may exist in an environment where there is only one vertical level in the fabricator or where there are no toolPods located in a vertical orientation where at least a portion of a toolPod lies above another in a vertical direction. Alternatively, whether in only one vertical level or in multiple levels of a cleanspace fabricator type whether vertically deployed or not there may be novel embodiments of the inventive art herein that involve collections of toolPods that are functional to produce on a portion of a process flow or even a portion of a process but utilize the methods described for fabricators.

A component of an imaging system may be formed by the combination of multiple imaging elements into a system. The combination may define an array of elements that is regular or non-regular. The imaging elements may each have the ability of emitting light, or ions or chemical species from their structures unto a neighboring substrate which may have a material or layer of material in a proximate location to the imaging elements such that it may receive the emitted light, ions or chemical species onto its surface or bulk.

An imaging system may be formed by the combination of a component of an imaging system as just discussed and a fixture to hold a substrate. There may also be alignment features on the substrate or on the fixture that may hold the substrate that may be operant to the function of the imaging system. There may also be a controller which may provide control signals to other components of the imaging system. The controller may also receive signals from other components of the imaging system. The controller may process a software algorithm or a program. In the processing by the controller, the controller may access data files stored within the controller or communicated to the controller by communication means.

There may be methods for forming an imaging system or imaging system component. An imaging system element or component may be formed individually by a process. It may then be tested in an individual fashion for metrology aspects desired for imaging processing. A subset of those elements or components that have metrology results that are within a specification range may be selected. The selected components or elements may place proximate to a receiving substrate and arranged in a designed pattern across the receiving substrate. In some embodiments, the receiving substrate may be round in form and have a radius approximately one inch in diameter. The receiving substrate may have had electrical connection features defined upon its surface to mate up with the components or elements that are placed thereupon. A process step to electrical connect an element to the substrate may be performed. Thereafter, the combined imaging elements may form an imaging system component that may be tested. The imaging system component may be placed proximate to a test substrate which has a layer or material that may be sensitive to electrons, ions or chemical species that may be emitted by the imaging system component. The imaging system component may next be rastered across the test surface to impart the image to the test substrate. The test substrate may be further processed such that a metrology process may be performed upon it to calibrate the imaging system component. The calibration data may be fed to a controller and the imaging system component may be included into a processing system which may be referred to as an imaging system. Thereafter, the imaging system may be used to process an image for a production substrate.

In another embodiment, the imaging elements may be formed and processed simultaneously. Techniques used for semiconductor and MEMS production may be used to create the array of imaging features on a substrate. A finished substrate with attached imaging elements may next be tested in concert with a test structure. The test structure in some embodiments may be a test wafer which may have been coated with a sensitive layer that may be sensitive to processing by the imaging elements. The resulting image structures on the test wafer may next be measure by a metrology apparatus. Comparison of the image test structure to a model may be performed to determine calibration and correction data values for the imaging system to use. Optionally a second test wafer may be processed with a repeat of the processing steps for the first test substrate but with correct values based on metrology. Next, the imaging system may be used to process an image for a production substrate.

In another embodiment, an imaging system may be formed by combining an imaging system component comprising a multiplicity of individual imaging elements. In some embodiments, the imaging system component may be formed in a round form factor common for semiconductor processing as wafers. The imaging system component may be included with other components including a wafer holding and alignment system and a controller to control the operation of the various components, collect data and run programs to construct the data into model corrections for the imaging system component. The imaging system components may be included into a processing tool that may be configured in a toolPod structure which itself may be capable of interfacing with a tool chassis structure. The toolPod comprising the imaging system may be optionally placed within a cleanspace fabrication environment. In the same environment a second toolPod may be placed and may be located at a level that may be vertically above the first tool location. A first substrate may be placed within the cleanspace fabricator. The substrate may be moved to the first toolPod with the imaging system and an imaging process may be performed upon the substrate. The substrate may next be moved to the second toolPod, and a second process may be performed by the tool in the second toolPod. In some embodiments this method may be used to process semiconductor or integrated circuit substrates, MEMS, optoelectronic, biomedical engineering substrates or the like.

In some embodiments a method for producing an imaging system may be to use a cleanspace fabricator to produce an imaging system according to the inventive art herein. In a first step a substrate may be placed within a cleanspace fabricator. The substrate may be moved to a processing tool which in some embodiments may be located within a toolPod. Next a processing step may be performed within the processing tool. The processing step may be part of a full processing flow designed to produce the array of imaging elements that form an imaging system component. After the full processing the imaging elements may be tested by their use upon a test substrate. After the test substrate with imaged material is further processed structure that may be measured may be formed. Next a metrology process may be performed to determine calibration data and offsets or adjustments. Thereafter the produced imaging system may be used to process a substrate to image a production pattern onto the substrate with an imaging sensitive layer.

One general aspect includes an imaging apparatus including: a first apparatus including a first substrate with a multitude of imaging elements arrayed thereupon where the imaging elements are capable of emitting an imaging signal from their structure to a material sensitive to their emissions on a surface in a vicinity of the first apparatus.

Implementations may include one or more of the following features. The imaging apparatus including the imaging apparatus and additionally including: a support component for a second substrate to be processed by the imaging apparatus; an alignment feature and alignment apparatus to measure the alignment feature; and a processor operant to collect data from imaging apparatus components, process the data and control imaging apparatus components based on the data. The imaging apparatus where the multitude of imaging elements emit electrons. The imaging apparatus where the multitude of imaging elements emit photons. The imaging apparatus where the multitude of imaging elements emit molecules. The imaging apparatus where there are more than 100, 1,000, 10,000, 100,000 or 1,000,000 imaging elements upon a substrate which may be planar. The imaging apparatus where the planar substrate is approximately round with a radius approximately one inch in dimension. The method additionally including: testing the imaging system to form test structures, measuring the test structures, and calculating correction values utilizing result of the measuring. The method where the imaging system includes more than 10,000 individual imaging elements. The method where the imaging system is approximately round in form with a radius of approximately 1 inch. The method additionally including the step of: including the imaging elements into a toolPod. The method additionally including steps of: placing the toolPod upon a chassis, where the chassis is part of a cleanspace fabricator; placing a second substrate into the cleanspace fabricator; placing an imaging sensitive film upon the second substrate; and performing an imaging process upon the imaging sensitive film upon the second substrate. The method where the imaging elements emit electrons. The method where the imaging elements emit photons. The method where the imaging elements emit molecules. The method where there are more than 10,000 imaging elements upon a first substrate. The method where the first substrate is approximately round with a radius approximately one inch in dimension.

One general aspect includes a method of forming an imaging system including: forming an individual imaging system element, testing the individual imaging system element, selecting the individual imaging system element based on compliance to desired specifications, forming a receiving substrate with electrical interconnect features thereon, placing selected individual imaging system elements upon the receiving substrate, and processing the placed selected individual imaging elements to electrically connect them upon the receiving substrate.

Implementations may include one or more of the following features. The method additionally including: testing the imaging system to form test structures, measuring the test structures, and calculating correction values utilizing result of the measuring. The method where the imaging system includes more than 10,000 individual imaging elements. The method where the imaging system is approximately round in form with a radius of approximately 1 inch. The method additionally including the step of: including the imaging elements into a toolPod. The method additionally including steps of: placing the toolPod upon a chassis, where the chassis is part of a cleanspace fabricator; placing a second substrate into the cleanspace fabricator; placing an imaging sensitive film upon the second substrate; and performing an imaging process upon the imaging sensitive film upon the second substrate. The method where the imaging elements emit electrons. The method where the imaging elements emit photons. The method where the imaging elements emit molecules. The method where there are more than 10,000 imaging elements upon a first substrate. The method where the first substrate is approximately round with a radius approximately one inch in dimension.

One general aspect includes a method for forming an imaging system including steps of: placing a second substrate within a cleanspace fabricator, moving the second substrate within the cleanspace fabricator to a processing tool within a first toolPod, processing the second substrate to form imaging elements upon the substrate, and moving the second substrate with imaging elements thereon out of the cleanspace.

Implementations may include one or more of the following features. The method where the imaging elements emit electrons. The method where the imaging elements emit photons. The method where the imaging elements emit molecules. The method where there are more than 10,000 imaging elements upon a first substrate. The method where the first substrate is approximately round with a radius approximately one inch in dimension.

One general aspect includes an imaging apparatus where the imaging apparatus includes a first substrate with a multitude of imaging elements arrayed thereupon. The imaging elements may be capable of emitting an imaging signal from their structure to a material sensitive to their emissions on a surface in a vicinity of the first apparatus. The imaging elements may be formed as field emission tips formed into silicon deposited into trenches. This deposited silicon when isolated from its surrounding materials such as dielectrics and insulators may be a filament of silicon. The emission tips may protrude from a backside of a base layer into a front-side of which the trenches are etched. That is a base layer may be etched through a front surface to form blind holes called trenches in the base layer. These trenches may be filled with various films. The base layer may be delayered from the opposite side or backside exposing the dielectric surrounded trench polysilicon filaments. In some examples, there are more than 1000 emission tips in the first apparatus. In some examples, a support component for a second substrate to be processed by the imaging apparatus is included as part of the imaging apparatus. In some examples, an alignment feature may be present on each of the imaging elements and a holder of the second substrate. The alignment apparatus may measure the alignment feature to register relative alignment. The apparatus may include a processor operant to collect data from imaging apparatus components, process the data and control imaging apparatus components based on the data.

Implementations of the imaging apparatus may also include one or more of the following features. The imaging apparatus may further include a cooling device in thermal communication with the second substrate. The imaging apparatus may further include a piezoelectric actuating device to raster the imaging apparatus. The imaging apparatus may function by rastering the imaging elements where this rastering includes at least ten steps within a distance separating two of the emission tips. In some examples the imaging apparatus may include electrical circuits that bias the field emission tips and these electrical circuits may be fabricated in a high voltage CMOS processing flow. The imaging apparatus may cause the electrical circuits to function where a bias potential that the electrical circuits applies causes an electro-potential bias of the tips to exceed 5 volts. In further examples, the bias may exceed 25 volts. In some examples, the fabrication of an imaging apparatus may start with a prefabricated embedded dram memory device which is further processed to expose an array of emission tips after further processing.

One general aspect includes a method of forming an imaging system including forming two or more individual imaging system elements. The method of forming the two or more imaging system elements may include etching a plurality of trenches into a base layer. The method may also include partially filing the trenches with conformal dielectric films. The method may also include filling the trenches with polysilicon. The method may also include finishing processing of an integrated circuit with metal layers. The method may also include processing the integrated circuit to thin a backside of the base layer, where the thinning exposes a dielectric film of one or more dielectric films which coat the polysilicon. The method may also include removing the one or more dielectric films to reveal polysilicon filaments. The method may also include etching the polysilicon filaments to form tips. The method may also include testing two or more of the individual imaging system elements. The method may also include selecting two or more of the individual imaging system elements based on compliance to desired specifications. The method may also include forming a receiving substrate with electrical interconnect features thereon. The method may also include placing two or more selected individual imaging system elements upon the receiving substrate. The method may also include electrically connecting two or more individual imaging elements to electrically connect them upon the receiving substrate.

One general aspect includes an imaging apparatus including an array of emission tips, where the emission tips include polysilicon formed into cavities in a base layer, and where the emission tips are sharpened by an etching process. The apparatus may also include a dielectric layer surrounding the emission tips at least in a portion of the emission tips that is surrounded by the base layer. The apparatus may also include electrical circuits connected to each of the emission tips, where the electrical circuits bias the tips based on data related to an image.

BRIEF DESCRIPTION OF THE DRAWINGS

The accompanying drawings, that are incorporated in and constitute a part of this specification, illustrate several embodiments of the invention and, together with the description, serve to explain the principles of the invention:

FIGS. 3A, B—Illustrations of an embodiment of an individual imaging element.

FIGS. 4A, B—Illustrations of a simplified array of imaging elements to depict how a collection of imaging elements may be formed in exemplary embodiments.

FIGS. 8A, B—Exemplary depictions of an array of imaging elements and a close up view of an exemplary small sized imaging element.

FIGS. 9A, B—Exemplary depictions of an array of imaging elements and a close up view of an exemplary small sized imaging element.

DETAILED DESCRIPTION OF THE INVENTION

In patent disclosures by the same inventive entity, the innovation of the cleanspace fabricator has been described. In place of a cleanroom, fabricators of this type may be constructed with a cleanspace that contains the wafers, typically in containers, and the automation to move the wafers and containers around between ports of tools. The cleanspace may typically be much smaller than the space a typical cleanroom may occupy and may also be envisioned as being turned on its side. In some embodiments, the processing tools may be shrunk which changes the processing environment further.

Description of a Linear, Vertical Cleanspace Fabricator

There are a number of types of cleanspace fabricators that may be possible with different orientations. For the purposes of illustration, one exemplary embodiment includes an implementation with a fab shape that is planar with tools oriented in vertical orientations. An exemplary representation of what the internal structure of these types of fabs may look like is shown in a partial cross section representation in FIG. 1. Item 110 may represent the roof of such a fabricator where some of the roof has been removed to allow for a view into the internal structure. Additionally, items 120 may represent the external walls of the facility which are also removed in part to allow a view into external structure.

Figure 1:
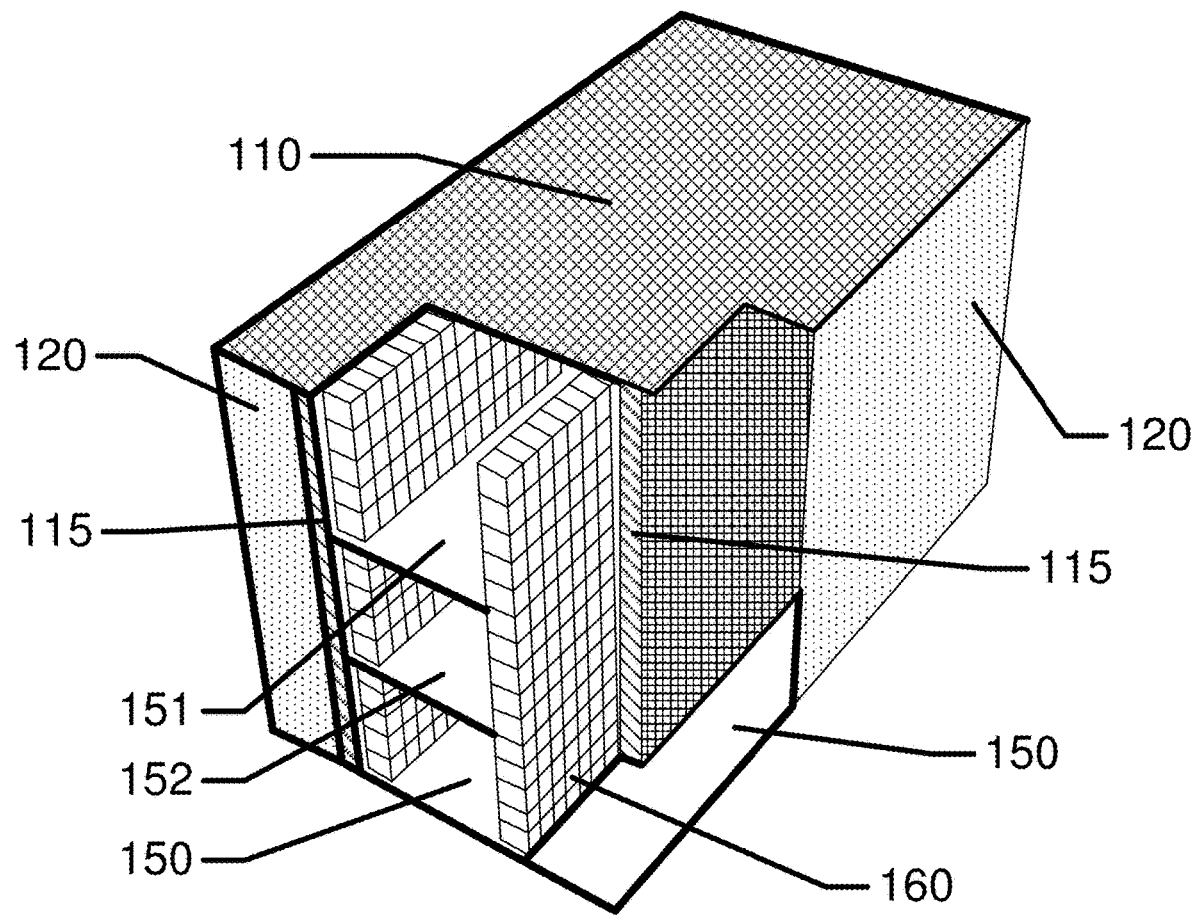
FIG. 1—An illustration of a small tool cleanspace fabricator in a sectional type representation.

In the linear and vertical cleanspace fabricator of FIG. 1 there are a number of aspects that may be observed in the representation. The "rotated and shrunken" cleanspace regions may be observed as cleanspace regions 115. The occurrence of cleanspace regions 115 on the right side of the figure is depicted with a portion of its length cut off to show its rough size in cross section. The cleanspaces lie adjacent to the tool pod locations. Depicted as item 160, the small cubical features represent tooling locations within the fabricator. These locations are located vertically and are adjacent to the cleanspace regions (115). In some embodiments a portion of the tool, the tool port, may protrude into the cleanspace region to interact with the automation that may reside in this region.

Floor 150 may represent the fabricator floor or ground level. On the right side, portions of the fabricator support structure may be removed so that the section may be demonstrated. In between the tools and the cleanspace regions, the location of the floor 150 may represent the region where access is made to place and replace tooling. In some embodiment, as in the one in FIG. 1, there may be two additional floors that are depicted as items 151 and 152. Other embodiments may have now flooring levels and access to the tools is made either by elevator means or by robotic automation that may be suspended from the ceiling of the fabricator or supported by the ground floor and allow for the automated removal, placement and replacement of tooling in the fabricator.

Description of a Chassis and a toolPod or a Removable Tool Component

In other patent descriptions of this inventive entity (patent application Ser. No. 11/502,689 which is incorporated in its entirety for reference) description has been made of the nature of the toolPod innovation and the toolPod's chassis innovation. These constructs, which in some embodiments may be ideal for smaller tool form factors, allow for the easy replacement and removal of the processing tools. Fundamentally, the toolPod may represent a portion or an entirety of a processing tool's body. In cases where it may represent a portion, there may be multiple regions of a tool that individually may be removable. In either event, during a removal process the tool may be configured to allow for the disconnection of the toolPod from the fabricator environment, both for aspects of handling of product substrates and for the connection to utilities of a fabricator including gasses, chemicals, electrical interconnections and communication interconnections to mention a few. The toolPod represents a stand-alone entity that may be shipped from location to location for repair, manufacture, or other purposes.

Imaging Apparatus

Figure 2:
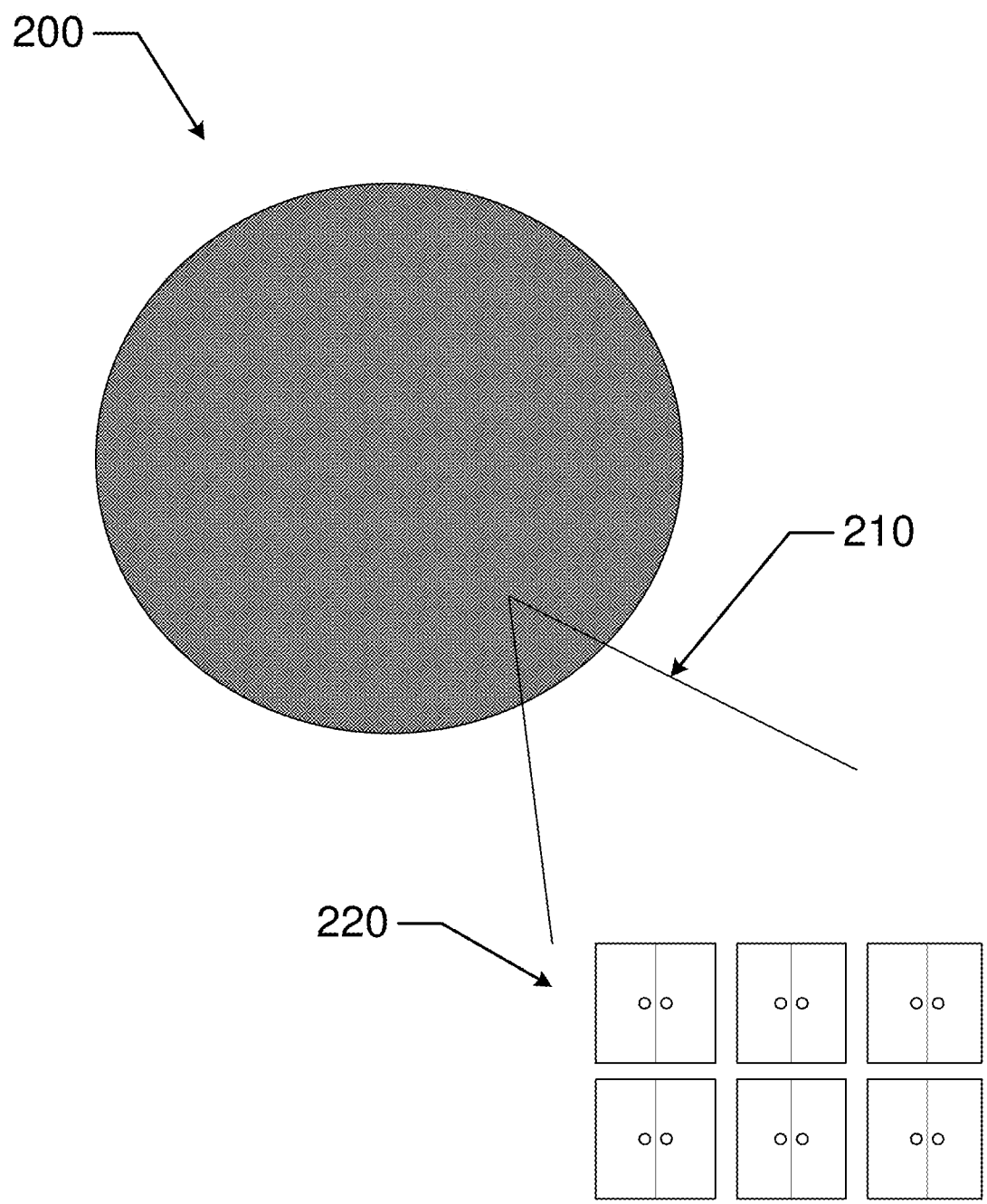
FIG. 2—An illustration of a full substrate imaging apparatus with highlighted regions illustrated at higher scale to depict a collection of individual imaging elements.

An imaging apparatus of various types may be used in the various cleanspace fabricator designs that have been described herein and in other referenced applications. Referring to FIG. 2 at item 200 an exemplary imaging apparatus in the exemplary form factor of a round substrate is depicted. In some embodiments, the imaging apparatus may be comprised of a large number of similar elements. As shown in a magnified view 210, the individual elements may be arranged in a regular pattern 220.

Referring to FIG. 3A at item 300 a close up of an imaging element may be depicted in cross section and FIG. 3B at item 350 a plan view. In some embodiments, the imaging element may be as simple as a stylus or probe needle. In the depiction of item 300 two stylus type elements may be located in one imaging element location; however more complicated elements may be preferred. In some embodiments, having two or more components on a single imaging element may allow for redundancy and methods of operating when one of the imaging elements 310 or 320 may be or may become defective for some reason. At 350, the exemplary imaging element may be demonstrated with electrical connections and interconnection elements. Item 360 may represent an electrical connection for imaging element 310. Item 360 is also shown in cross section and may have a thru-via 330 and an interconnection feature 340 electrically connected to it. As well, other electrical connections 345 may also be connected to the substrate upon which the imaging element is configured.

There may be many different manners to form imaging elements in an array on a substrate. For example, the techniques and equipment used to process semiconductor substrates to form metal connections and interconnections such as vias may be used to form the features in the exemplary imaging elements depicted at 300. A stylus head may be formed by various chemical etching techniques, for example. Processes to form imaging apparatus may typically have degrees of error associated with their formation.

Referring to FIG. 4A, imaging array 410 may represent a simplified exemplary array of imaging elements. The array may depict nine such imaging elements. The element of item 420 may have an error of location in both of two orthogonal coordinates. The space depicted at 421 may represent the vertical error of location from an idealized equivalent spacing of the nine array elements. The space at 422 may represent the horizontal error of location.

The imaging element at item 430 may also have errors of location in different directions as depicted. In fact, all of the elements may have random amounts of error in location. In some embodiments, the errors may be sufficiently small to be within a technological need for the imaging element. In other embodiments, errors of production of an imaging array or variation of the calibration of the imaging system may be sufficiently large to require correction. In FIG. 4B, item 450 a depiction of test structures imaged into a test substrate by the imaging array 410 may be found. The aforementioned errors may be found as offset in the location of the test structure depiction 460. A test structure of the type in 450 may be formed by the imaging array and then characterized by metrology techniques. These measurements may be used to allow the imaging array to be utilized in methods that correct for errors in the characteristics of the array.

The imaging elements may be located in the grid pattern of imaging array 410 and this pattern may have an imaging element that may have a resolution capability of a small distance. In some embodiments, the small distance may be as small as 1-10 nanometers. The spacing between imaging elements may be depicted at 470 and 480. The spacing may be such to create a regular array, or in other embodiments may be designed in a non-regular fashion. This spacing may be a few hundred nanometers in some embodiments. In other embodiments the spacing could be a millimeter or more. In some embodiments, where the spacing is an exemplary 1 micron, the imaging array must be translated numerous steps in both a vertical and a horizontal direction. To cover the entire distance, the step pattern of the entire grid array (as a whole) might be 1,000 nanometers/10 nanometers or 100 steps in each direction as an example. By combining the calibration data the array may be controlled by a controller to write arbitrary, but defined in data forms, image patterns where the fundamental image element size may be 10 nanometers by 10 nanometers in size. As mentioned, these values are provided in an exemplary manner and the use of an imaging array with multiple elements may function similarly for numerous embodiments. When various imaging elements have errors of location as discussed these imaging location errors may be corrected algorithmically.

In an exemplary embodiment, the imaging device may be characterized by metrology and each individual imaging element characterized individually. In an example to describe a process related to this, a state of a detector may have errors that range from −10 nanometers to +20 nanometers in a first "X" coordinate direction and −20 to +20 nanometers in a second orthogonal "Y" direction. If the step resolution on the array is an exemplary 10 nanometers between each step that moves the array then to image the full space, the array may be stepped 1 extra time for the negative X correction, 100 times for the normal area to be imaged, and then 2 additional times for the positive X Correction. This scanning procedure may repeat each time a Y direction is stepped. The Y steps may be stepped an extra 2 times for the negative Y correction, 100 times for the normal area to be imaged and then an extra 2 additional times for the positive Y correction. Each image element may have its own correction and at the extremes of the stepping process it may be expected that only a few of the elements would be active. This process is described for exemplary purposes and each imaging system may have a different set of calibration requirements. And in some cases, the elements of an imaging array of the type described herein may have a degree of dynamic characteristic and therefore repeated calibrations may be required as the apparatus is used.

In a further exemplary vein, an array according to the descriptions herein may comprise an apparatus that has a radial dimension of an inch or approximately 25 mm. The surface of such an imaging device may therefore have approximately $(3.14)*25*25$ mm$^2$ or approximately 1960 mm$^2$. If the imaging arrays have an exemplary 10 micron distance between elements and a resolution size of 10 nanometers, then scanning may involve a default 1000 steps in each of the X and Y directions plus any required extra steps for calibration needs. As well if each imaging element covers a 100 micron square area of a surface then each millimeter square would have 10,000 such elements therein. The entire array may comprise 19,600,000 elements. Such an array might be able to be fabricated using the tools of semiconductor manufacturing as an example. That many elements may be expected to have numerous defective elements either initially or after use. There may be a utility to creating redundancy at each element location for this purpose. As well, it may be useful to invoke processes that significantly over scan a single imaging element dimension to allow for the ability of correcting for element areas that are non-functional.

The calibration of array elements may also involve calibration of the intensity of the imaging signal of each element. In array designs where each element may have an alterable intensity of operation, the calibration result may create a set of individual intensity settings that may be applied to each element. In other designs the dwell time at each step cycle may be made to allow for the least intense element to deliver an appropriate imaging signal. In such a case, the individual elements may operate in a digital fashion toggled on and off on an individual basis to deliver a required imaging signal.

Figure 5:
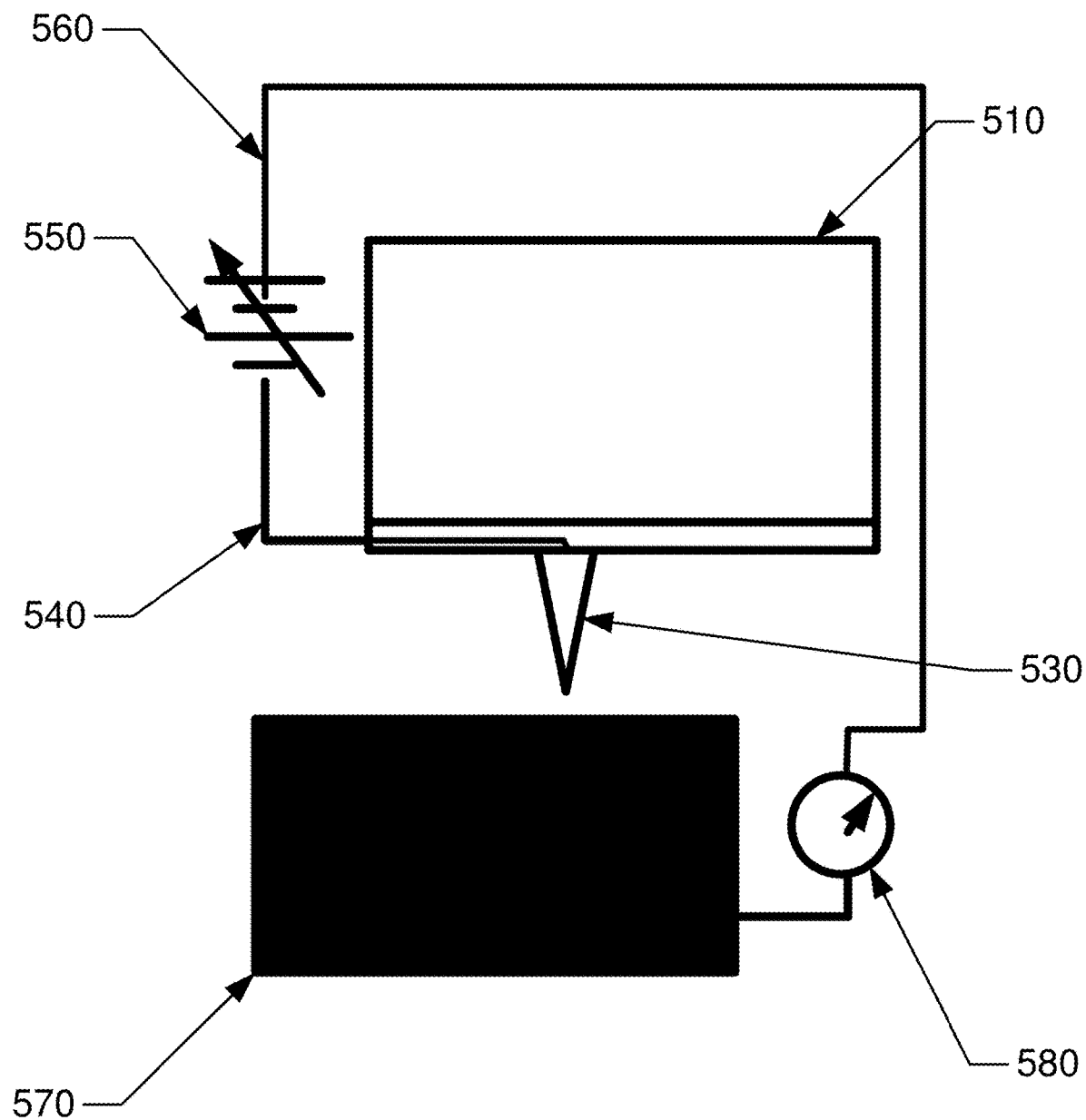
FIG. 5—A depiction of an embodiment of an exemplary positioning element.

Referring to FIG. 5, a probe type element 510 may also be useful to measure a dimension of an array of imaging elements from the surface of the substrate that the imaging array will image. In some embodiments, it may be useful to calibrate and adjust the imaging array apparatus in separation from a substrate to be imaged. In FIG. 5, a distance of a probe tip 530 from a conductive surface of an element body 570 may be measured based on an electrical signal. In some embodiments, the electrical signal may be based on electric emission from the probe needle biased to a certain potential. The emission signal may be characteristic of the separation of the needle from the conductive surface. There may be numerous other techniques that may be useful in calibrating distances including electrical signals from tunneling processes across a gap and AFM type force metrology based on the establishment of a force signal as a needle interfaces with a surface. Other techniques relating to optical signals may also be used to calibrate a height of the imaging array above a target substrate.

Continuing with an emission current embodiment, the probe tip 530 may be biased by a variable voltage supply 550 which may be connected to the probe tip 530 with an interconnect 540 and to a conductive surface of an element body 570 with another electrical interconnect 560. Electrical current may flow from the probe tip 530 across a calibrated gap to a conductive substrate and through a current measuring apparatus 580. A combination of sensitive measurement devices may be used to keep a leveled distance relationship in place across a substrate of imaging elements. The element body 570 may be part of the substrate to be imaged or it may be part of a calibrated holding apparatus that holds the substrate in a calibrated fashion. In some embodiments, the thickness of the substrate may be a parameter that may need to be collected for calibration. As may be apparent, in embodiments where the distance of the imaging elements to the imaged surface is critical it may be important to keep the imaging apparatus at a stable and uniform temperature across its extents and over time periods.

Figure 6:
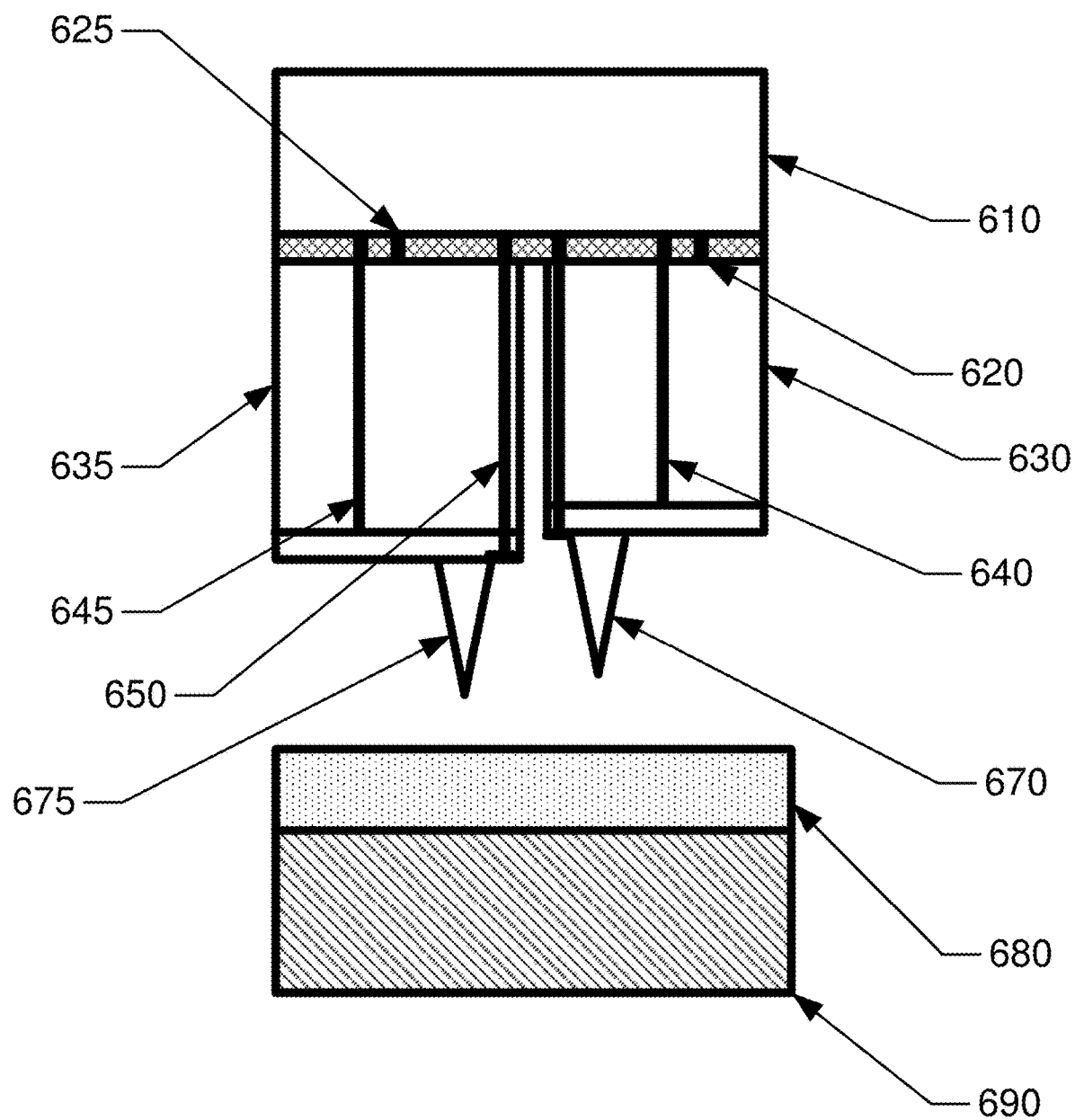
FIG. 6—A depiction of an embodiment of a redundant imaging element.

Referring to FIG. 6, an example of a redundant imaging element 610 is depicted. The element may configure two copies of an active element. In other embodiments there may be more than two elements. In an example embodiment, the imaging elements may be formed upon a substrate that may be controlled for its thickness. For example, the substrates 630 and 635 may be comprised of a piezoelectric crystal. Piezoelectric crystals may have the property of expanding along a structural axis in response to an electric field being applied across the crystal the electrical fields may be applied in an exemplary fashion across interconnects 620 and 640. The active element 675 may be moved into an imaging position by the application of a potential voltage across 625 and 645; whereas the redundant element 670 may remain withdrawn and not activated. In other embodiments, the redundant element may be made nonfunctional by other means than physical location, including in a non-limiting sense not being energized.

The active element 675 may be used to expose a chemically active layer 680 and a substrate 690. In some embodiments the exposure may comprise electron bombardment based on emission current emitted from the tip which may be biased through the electrical interconnect 650. In other embodiments the tip may be used to create an electric field at the surface that may be used to direct ionic species towards the chemically reactive layer. In still other embodiments, the narrowed tip may comprise a photon directing material that may be coated with a reflecting material such as a metallic film, except at the very tip. The tip may direct light from a light source such as a solid state laser or a light emitting diode to the substrate. In some additional embodiments, a tip structure may represent a nanolaser device. In still further embodiments, the array may be configured with nanoscaled emitters. In some cases, nanoscaled emitters may be tuned to emit at wavelengths that are a fraction of the emitter dimensions or at sub-wavelength conditions. There may be numerous other types of imaging elements. Because an imaging array may have so many individual elements, the power requirements for each element may be very small. In some embodiments, the amount of time required for exposure of the entire surface may be very small.

Figures 7A, 7B:
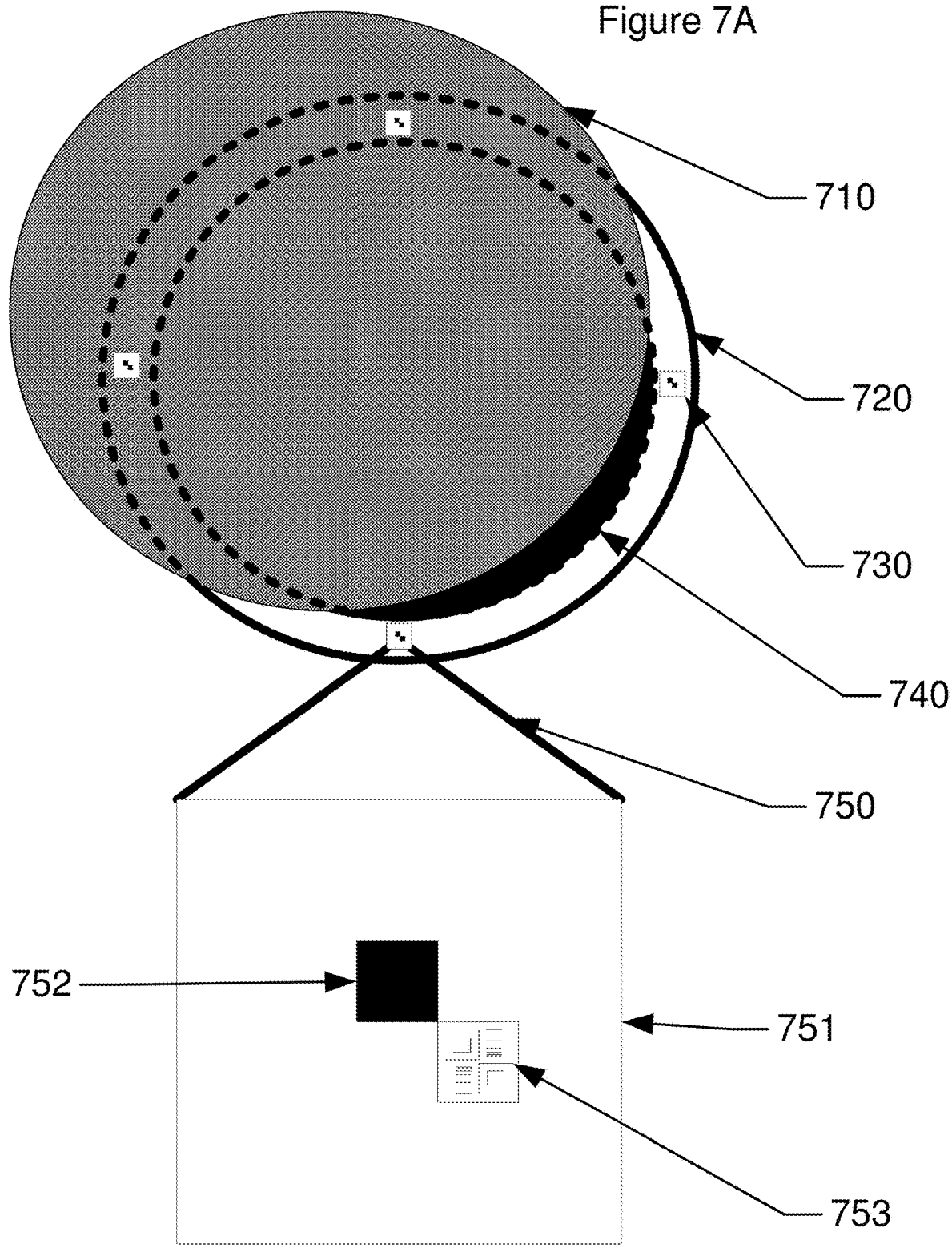
FIGS. 7A, B—Exemplary depictions of an imaging apparatus depicted partially offset from an exemplary location of operation in proximity to a substrate in a holding location with alignment features.

Referring to FIG. 7A, an imaging system may be displayed. Item 710 may represent an imaging component in the form of a round substrate. The items are demonstrated with some transparency in the illustration for illustration purposes only. The round substrate may be larger than a substrate to be imaged, 740. The substrate to be imaged may sit inside a pocket of a holding fixture 720. The holding fixture may have alignment features such as 730 incorporated into it. The alignment feature may include a flat metallic surface 752 useful for calibrating the height of the imaging component. In addition, it may have alignment features 753 that may be used in conjunction with scanning systems such as atomic force microscopy probes or the like to calibration location in the plane of an idealized substrate surface. A magnified representation of the alignment structures 750 may be found at 751 in FIG. 7B.

Referring to FIGS. 8A and 8B a more complicated imaging element may be illustrated. At FIG. 8A item 810 an exemplary array of nine elements such as item 825 may be found. Each of the elements may have at least one imaging elements 820. One of the imaging elements may be demonstrated in a close-up representation 830 at FIG. 8B which also may represent a cross sectional view. The exemplary imaging element may be capable of irradiating a target substrate with electrons or other ionic species. Item 840 may represent an exit slit that may be biased to a desired energy of an existing ion. The slit may insure that reasonably columnated ion beams emerge from the imaging element. Item 850, 860 and 870 may represent focusing elements for the beam. The electrons may traverse a column that may have these focusing elements deposited on its sidewalls. Item 880 may represent an initial imaging slit that may be used to accelerate ions or electrons from a filament or other source of ions or electrons 890. Numerous electrical connection points to the portions described are illustrated with circular connection points such as 881 and 882. These are for illustration purposes and may represent that one or more control signals or electrical signals may be connected to the various described portions.

An alternative type of micro imaging element may be found in reference to FIGS. 9A and 9B. At 9A, item 910, another exemplary array of nine elements such as 925 with an associated image element 920 may be found. One of the elements represented in the close-up 930 of FIG. 9B may be found. This element may be useful for ejecting nanoscaled droplets of chemical reactant to react with resist layers to form imaged layers. Item 990 may be an ejected chemical nanodroplet. Item 980 may be an element to eject a nanodroplet 975. A piezoelectric element 950 may be useful as such an ejection element or other such features as may be found in ink jet printing technology may be represented by 950. At 970 droplets of chemical may be moved by microfluidic techniques through the use of coated electrodes such as items 960 and 965. The electrodes may receive electrical control signals through interconnects from controlling systems. An example of such an electrical connect is depicted at 961.

Methods of Producing and Utilizing Imaging Systems

Figure 10:
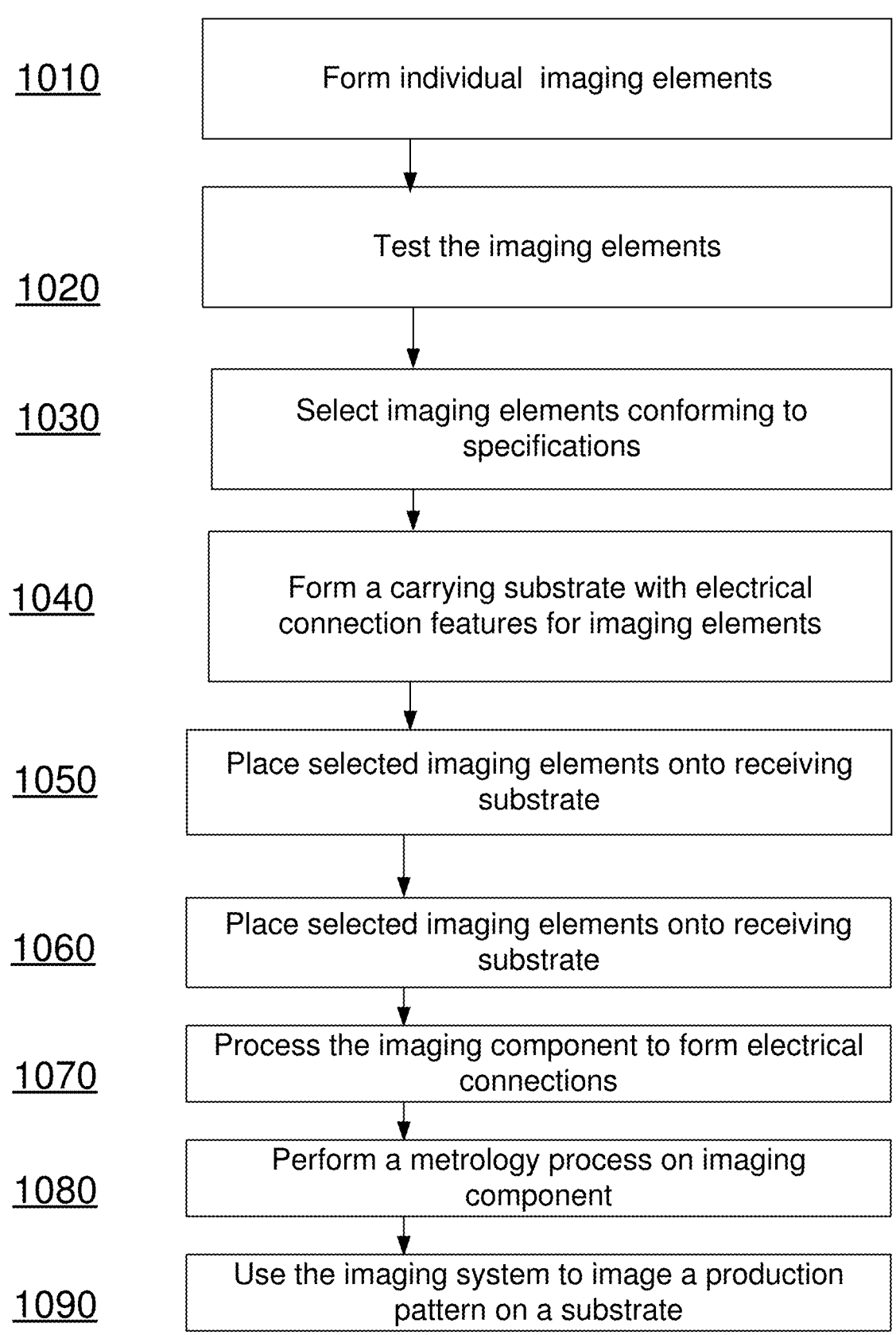
FIG. 10—A Flow chart depicting exemplary methods of production of an imaging apparatus.

Referring to FIG. 10, a method for forming an exemplary array of imaging elements may be found. At step 1010 an imaging component may be formed by processing or otherwise obtained. At 1020 the individual imaging components may be tested for their desired imaging properties. At 1030, imaging components that conform to a specification range may be selected from the population of imaging components. At 1040, a carrying substrate consistent to receive the numerous imaging elements may be formed and configured with electrical connection features such as solder bump. At 1050 the individual imaging components may be placed in receiving locations upon the carrying substrate. At 1060 the imaging component may be processed to electrically connect the imaging components. The apparatus that results at step 1060 may be further used or in other embodiments it may be obtained by a user and at 1070 the imaging system may be used to image a test pattern on a substrate with an imaging sensitive layer thereupon. At 1080, a metrology process may be performed on the substrate with the test pattern and calibration adjustments may be determined. At 1090 the imaging system may be used to image a production pattern on a substrate with an imaging sensitive layer thereupon.

Figure 11:
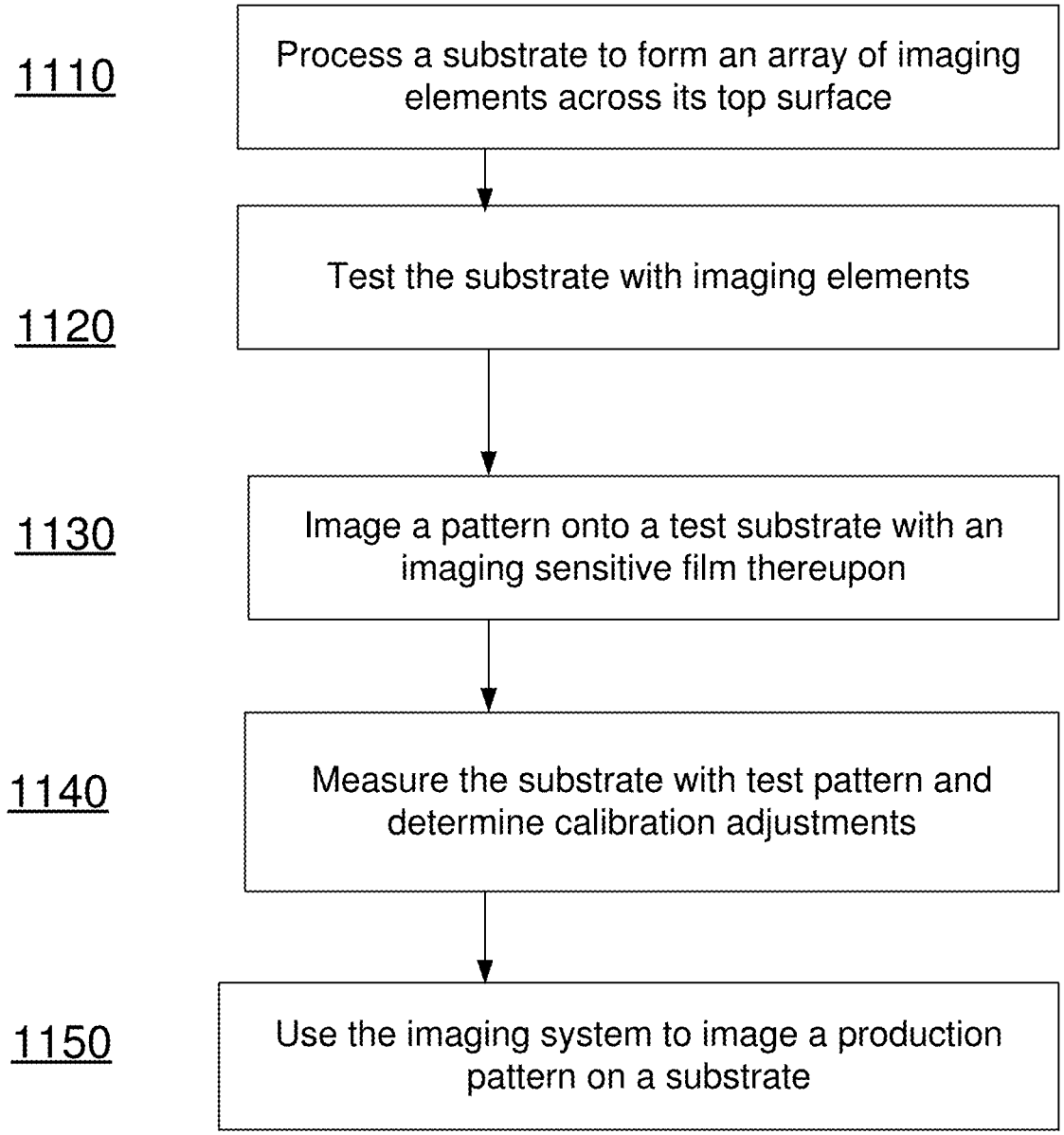
FIG. 11—A Flow chart depicting exemplary methods of production of an imaging apparatus.

Referring to FIG. 11, a method for a simultaneous processing of the imaging elements may be found. At step 1110 a substrate may be processed to form imaging elements upon the substrate such that the imaging elements are simultaneously formed across the substrate. At step 1120, the imaging components upon the substrate may be tested for their desired imaging properties. At step 1130, the imaging system may be used to image a test pattern on a substrate with an imaging sensitive layer thereupon. At 1140, a metrology process may be performed on the substrate with the test pattern and calibration adjustments may be determined. At 1150 the imaging system may be used to image a production pattern on a substrate with an imaging sensitive layer thereupon.

Figure 12:
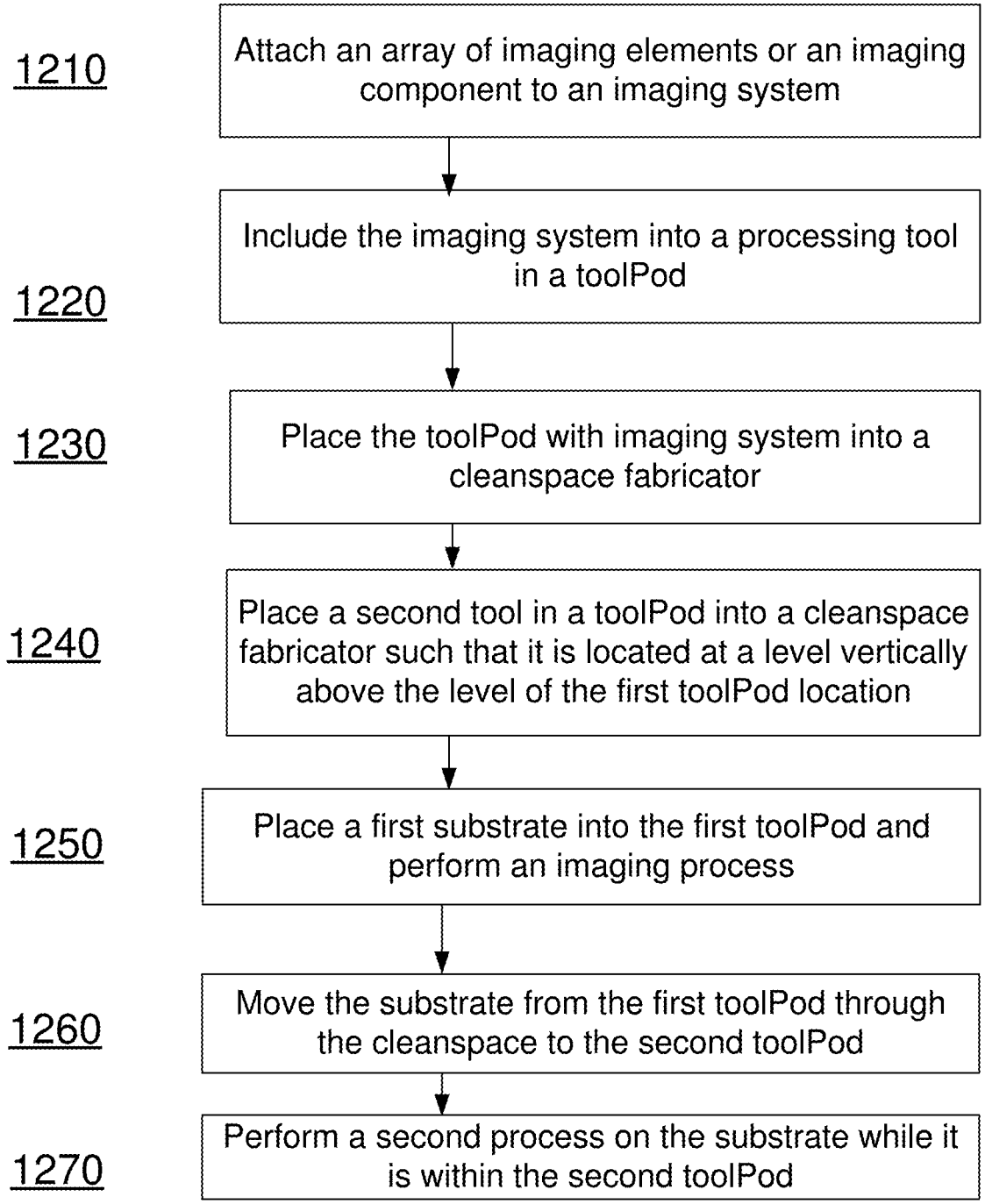
FIG. 12—A Flow chart depicting exemplary methods of utilization of an imaging apparatus.
Figure 13:
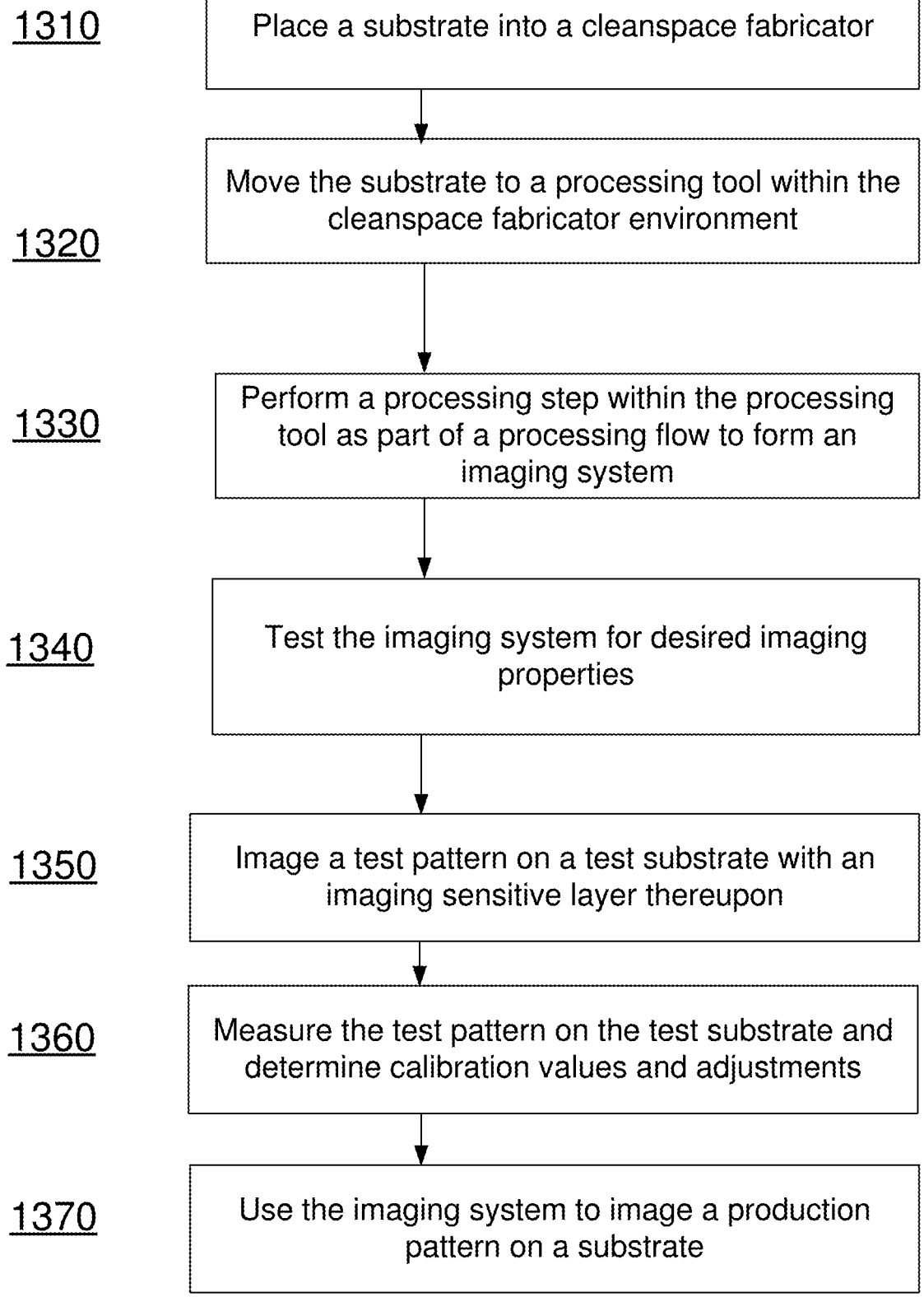
FIG. 13—A Flow chart depicting exemplary methods of production of an imaging apparatus.

Referring to FIG. 12 a method for using an exemplary array of imaging elements may be found. At step, 1210 an array of imaging components may be attached to an imaging system, which may optionally have a receiving recess to hold substrates to be imaged as well as alignment features upon a portion of the component with said recess. At step 1220 the imaging system may be including into a processing tool that is configured within a toolPod structure and capable of interfacing with a chassis structure to receive the toolPod. At step 1230, the toolPod may optionally be placed within a cleanspace fabrication environment. At step 1240 a second tool in a toolPod may be placed in a cleanspace fabrication environment wherein the second tool is located at a level that is vertically above the first tool location. At step 1250 a first substrate may be placed within the first toolPod and an imaging process may be performed by the imaging system. At step 1260, the substrate may be moved from the first toolPod to the second toolPod. At 1270 a second process may be performed by the tool in the second toolPod. There may be numerous types of substrates that may be processed according to the method of FIG. 12 including in a non-limiting sense a semiconductor processing, a microelectronic processing, an electronic component assembly processing, a MEMS processing and optoelectronic processing, Referring to FIG. 13, a method for producing an imaging system may be found. At Step 1310, a substrate may be placed within a cleanspace fabricator. At step 1320 the substrate may be moved to a processing tool. In some embodiments, the processing tool may be located within a toolPod. At step 1330 a processing step may be performed within the processing tool as part of a processing flow to form an imaging system. At step 1340, the imaging components upon the substrate may be tested for their desired imaging properties. At step 1350, the imaging system may be used to image a test pattern on a substrate with an imaging sensitive layer thereupon. At 1360, a metrology process may be performed on the substrate with the test pattern and calibration adjustments may be determined. At 1370 the imaging system may be used to image a production pattern on a substrate with an imaging sensitive layer thereupon.

Control Systems

Figure 14:
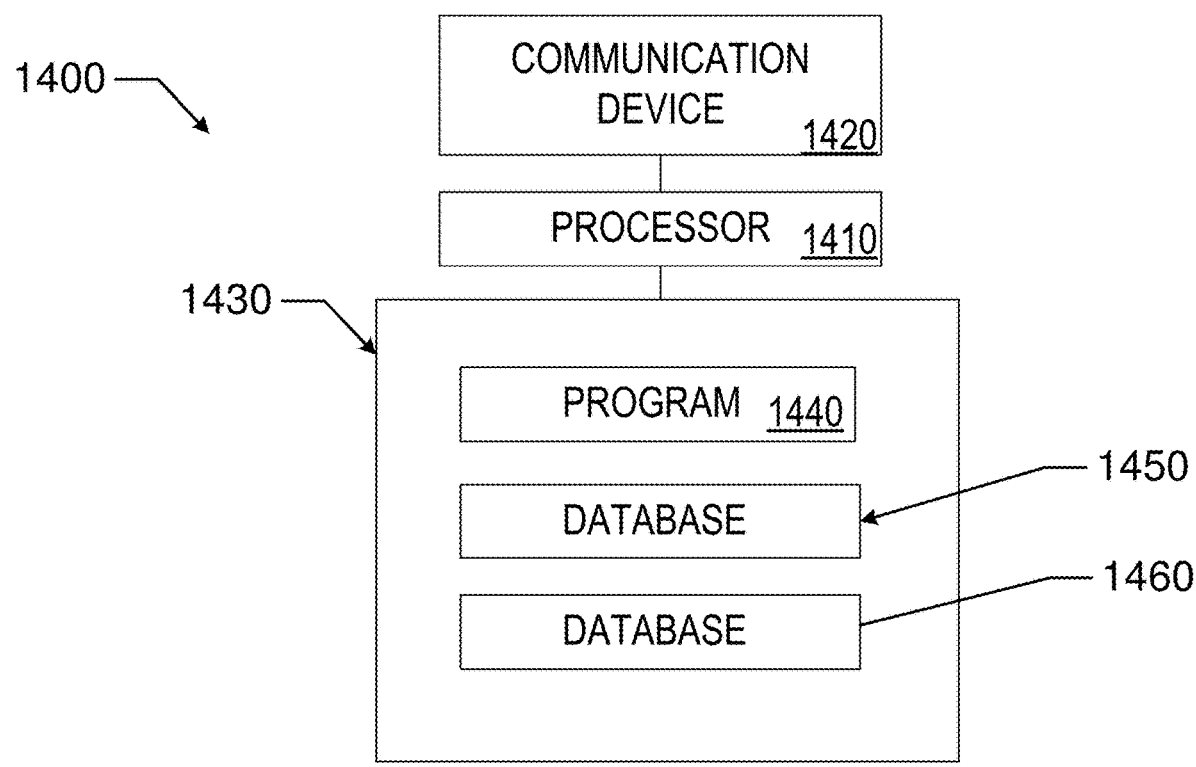
FIG. 14—An exemplary processor that may be useful for some embodiments of imaging systems.

Referring now to FIG. 14, a controller 1400 is illustrated that may be used in some embodiments of an imaging system. The controller 1400 includes a processor 1410, which may include one or more processor components. The processor may be coupled to a communication device 1420.

The processor 1410 may also be in communication with a storage device 1430. The storage device 1430 may comprise a number of appropriate information storage device types, including combinations of magnetic storage devices including hard disk drives, optical storage devices, and/or semiconductor memory devices such as Flash memory devices, Random Access Memory (RAM) devices and Read Only Memory (ROM) devices.

At 1430, the storage device 1430 may store a program 1440 which may be useful for controlling the processor 1410. The processor 1410 performs instructions of the program 1440 which may affect numerous algorithmic processes and thereby operates in accordance with imaging system manufacturing equipment. The storage device 1430 can also store imaging system related data, including in a non limiting sense imaging system calibration data and image data to be imaged with the imaging system. The data may be stored in one or more databases 1450, 1460. The databases 1450, 1460 may include specific control logic for controlling the imaging elements which may be organized in matrices, arrays or other collections to form a portion of an imaging manufacturing system.

Imaging Systems Using Deep Trench Processing

In the current state of the art Dynamic Random Access Memory DRAM processing and embedded DRAM process as well as other trench based processes have features that are consistent with the form of the novel imaging systems herein. In an example, a 22 nm. embedded dram process may have high voltage logic blocks in concert with dram trenches. In some examples the dram trenches may be microns deep into the silicon bulk. In some examples, the dram trenches may include capacitive films on the sidewall of the trench followed by filling with a conductive material, such as in a non-limiting perspective polysilicon. The polysilicon may be deposited in chemical vapor deposition processes that may allow for auto-doping of the polysilicon. The processing of the electrically connected trenches according to various processes currently developed may substantially comprise initial steps to form examples of the imaging systems described herein.

There may be some additional steps as well as some modifications to the processing of semiconductor processing trenches for applications such as dram capacitors. For example, for a doped polysilicon filled trench it may be desirable to have a higher doping concentration for an imaging application since current will be flowing through the polysilicon in a fairly constant manner as opposed to transient charging and discharging of the capacitor in memory applications. The insulating capacitive films that may surround the conductive polysilicon fill may be thickened to allow for passivation capable of withstanding higher bias conditions. For example depending on the material of the capacitive films, such as silicon oxide and silicon nitride or combinations thereof, the thickness may be increased such that a bias of up to 30 volts or more may be applied to create field emission current from a trench point, the dielectric films may be thickened to support that higher voltages.

Figure 15A:
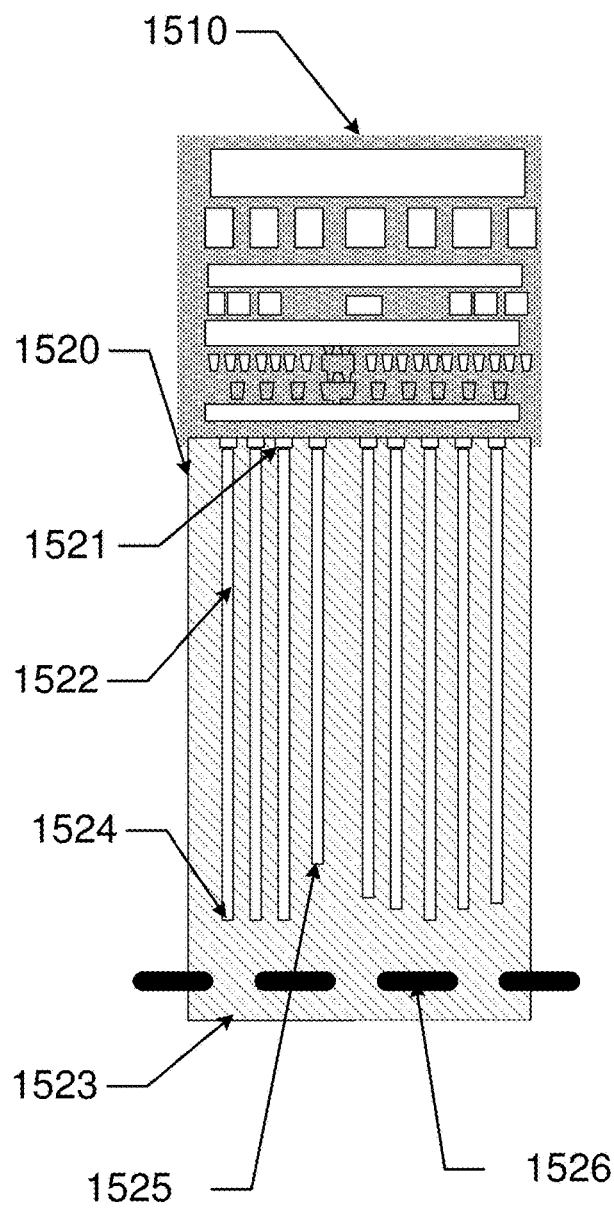
FIG. 15A—An exemplary cross section view of a processed substrate with deep trenches, a device layer in metal interconnects FIG. 15B—The exemplary item from FIG. 15A further illustrating isolation of trench elements.

Referring to FIG. 15A, a cross section of an integrated circuit with trench capacitors is illustrated. As mentioned previously, this may be any circuit type with trenches and in some examples may be a dram or embedded dram circuit. The embedded dram circuit may have more flexibility to bias the trenches to significant potentials. The metal layers 1510 may be depicted in the layers indicated by the shading around 1510. The trench layer may be located in a base layer 1520 which may comprise semiconductors or insulators in some examples. When the device is a dram or e-dram the base layer may be silicon and transistors 1521 may be located in the semiconductor. The semiconductor base layer may be very much thicker than the deep trenches 1522 as indicated by the dashed line 1526 and the bottom of the base layer 1523 where the dashed line indicates intervening material not illustrated. The base depth of the trenches may have variability as indicated by a deeper trench 1524 and a shallower trench 1525.

Figure 15B:
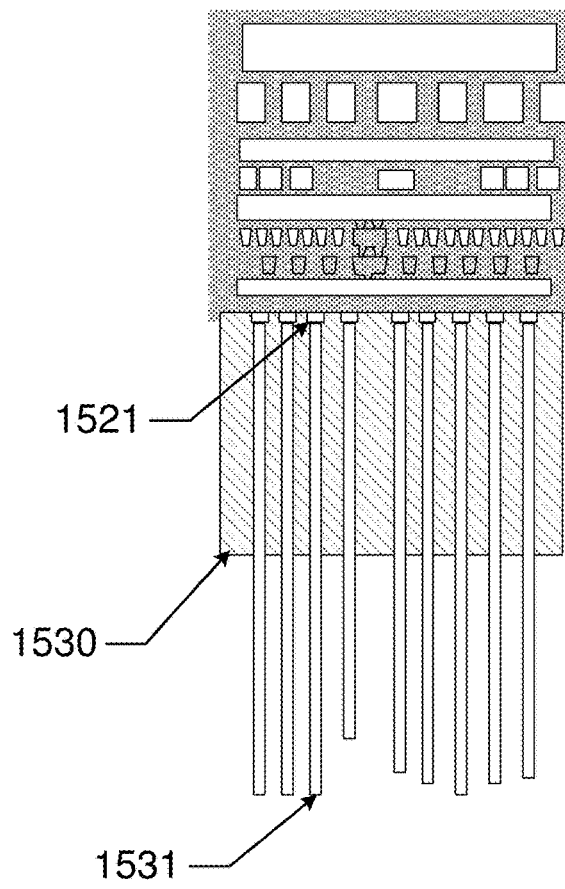
FIG. 15C—The exemplary item from FIG. 15B further illustrating wet chemical processing.
FIG. 15D—An exemplary cross section of a processed substrated with isolated trench filaments that have been sharpened for field emission points.
FIG. 15E—An exemplary cross section of the item from FIG. 15D in use to image a substrate with a sensitive layer.

In some examples according to the present invention further processing is illustrated by FIG. 15B. The base layer may be thinned by various means know in the art. For example, the semiconductor substrate may be back ground as a first step where bulk material may be ground off. After a significant amount of material is removed, another type of removal may be performed in particular where the removal is selective to the base material relative to the trench capacitor layer. In some examples the outermost trench capacitor layer may be silicon oxide. A wet chemical etch with hot phosphoric for example may remove silicon while not removing silicon oxide. Reactive Ion Etching may also include chemistry that is selective to silicon rather than silicon oxide. There may be numerous ways to thin the base layer 1530 as shown in FIG. 15B. In some examples there may be protective layers that are added onto the metal layers 1510 during the etching which may need to be removed. The result of a selective etch is that the trenches with their capacitor films may be isolated 1531 from the base layer.

Figure 15C:
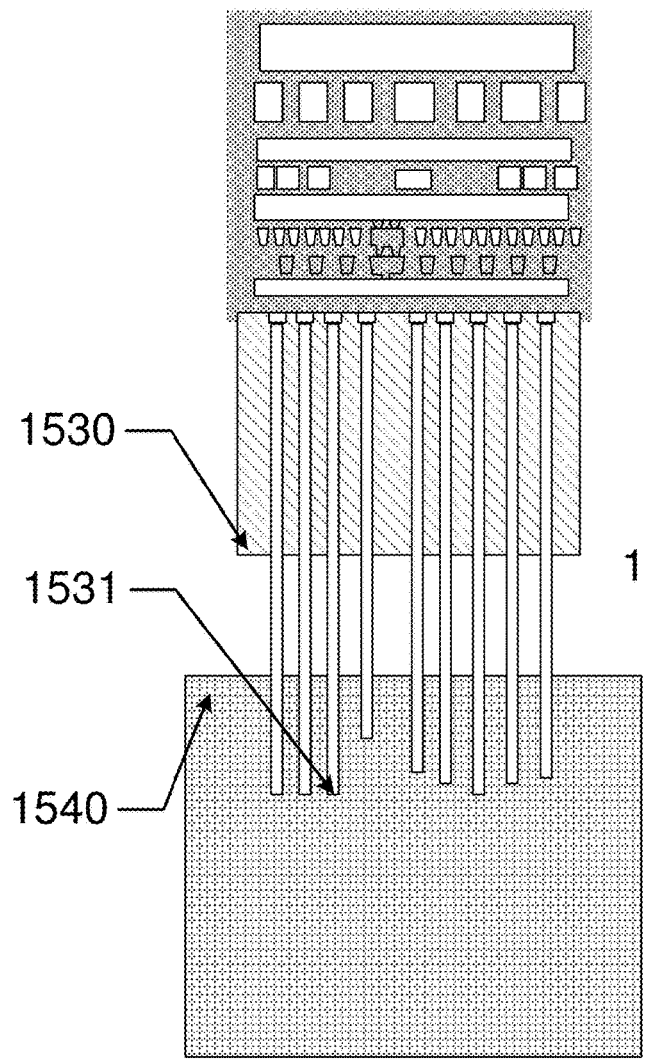
Figure 15D:
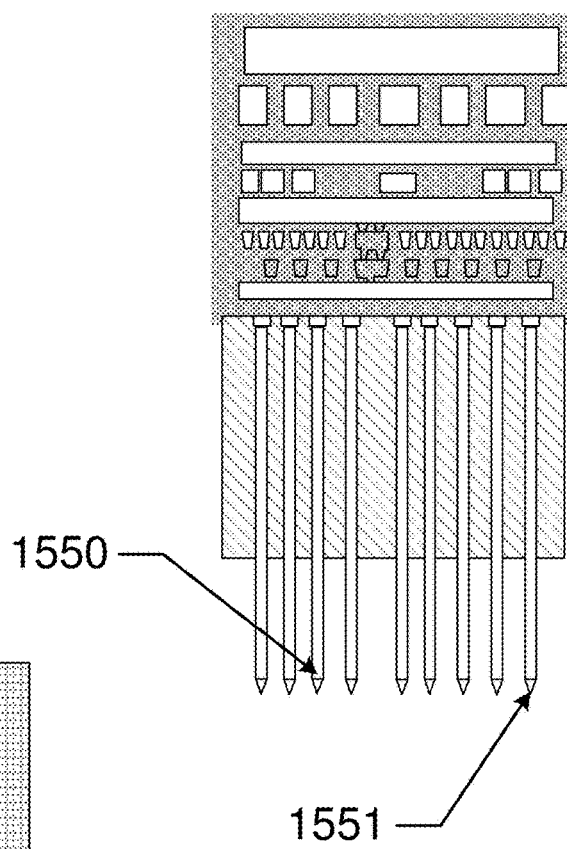

In some examples, after the trenches with their capacitors are isolated, the capacitor films may be removed at least to a level close to the remaining base layer 1530. Proceeding to FIG. 15C, an illustration of a wet chemical processing step may involve a bath 1540 of chemicals. As depicted the bath may allow a buffer between treated areas and the remaining base layer since the capacitor films may be useful to isolate the remaining processed trenches from the base layer which may be grounded in some examples. The capacitor films may be removed exposing the silicon in the trench. In some examples, the silicon thus exposed may next be processed in various etch processing to etch the silicon. In some electrochemical etches, the etch rate of the silicon may be enhanced by biasing the silicon. Such bias may be activated through the electronics layers of the integrated circuit. In some examples, the etch chemistry may be sensitive to the level of oxygen dissolved in the chemical. At the surface of the chemical, the ambient may have significantly higher levels of oxygen and the dissolved layers may be significantly higher therefore at the surface of the layer. This may create an accelerated etching of the chemistry or electrochemistry to form a sharp point by necking down the silicon. Proceeding to FIG. 15 D the sharp, emission points 1551 may be formed in the isolated trench material 1550. In may also be possible in some examples to even out the heights of the emission points through the processing since all of the trenches will neck down at a common surface layer of the wet chemical.

Figure 15E:
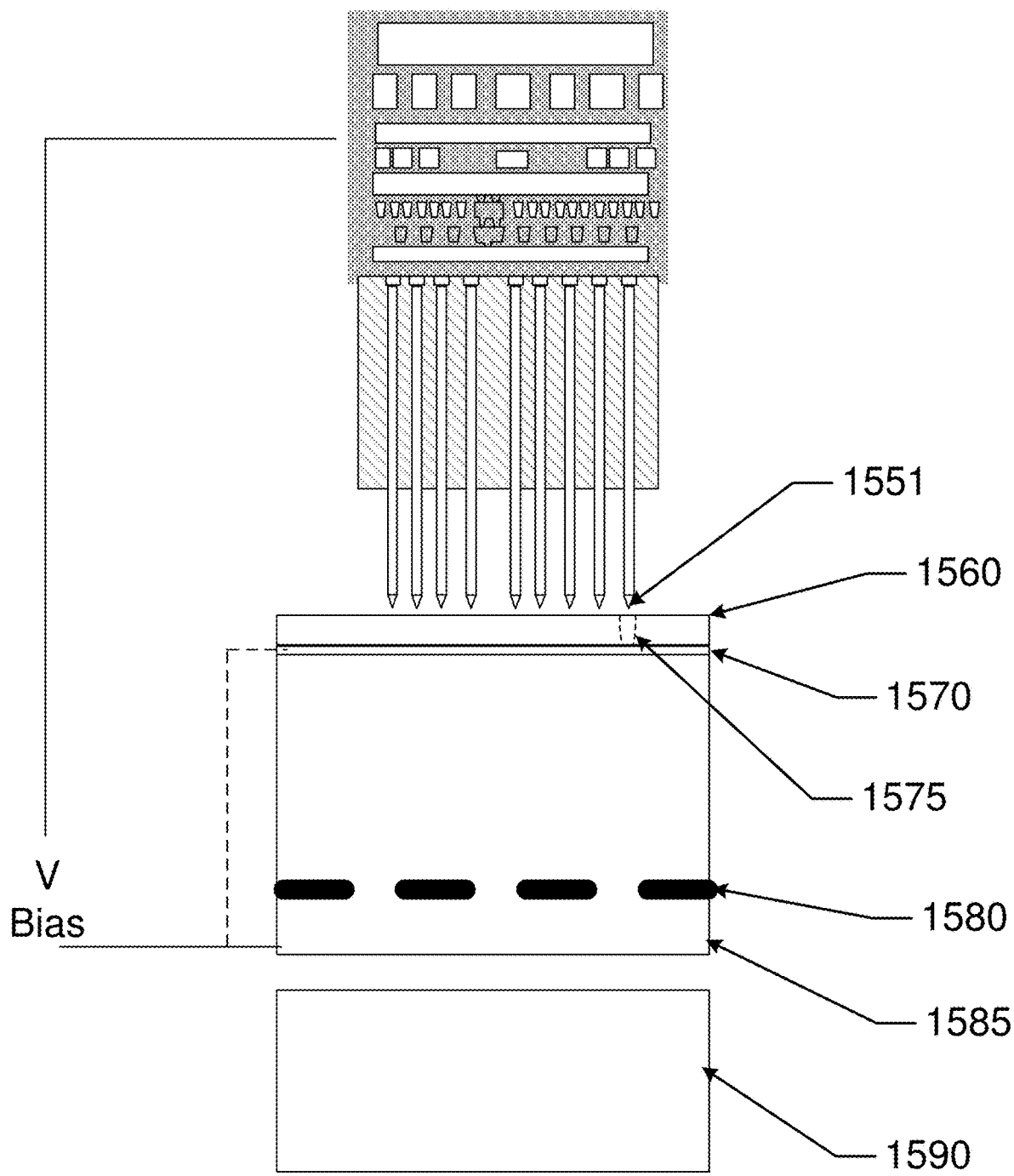

Proceeding to FIG. 15E, an example of utilizing the resulting trench points as emission sources for imaging is illustrated. The electronics of the circuit may be useful to bias the emission points independently based on data provided to the electronics The data may be communicated by various types of wired and wireless transmission. It may be possible to have an extremely large number of imaging sources with the techniques described. Therefore, the rate of imaging may be very high. As well, the amount of power delivered to the imaged substrate 1585 (where the dotted line 1580 indicates a gap in the material illustrated) may be very large. Therefore, there may be active cooling means 1590 attached to the substrate while the emission based imaging occurs. The imaging may be made to a substrate which may have an electron sensitive "lithography" resist 1560 applied to it. It may be important to remove charge during the emission process and an electro-conductive layer 1570 may be applied underneath the lithography resist. In some examples, titanium nitride which is commonly used in lithography processes may be sufficiently conductive, Referring to FIG. 15 E, the emission from an emission point 1551 may occur from the sharp point on the tip into an imaged region of the resist 1575. In some examples, the tip may be much smaller than the dimension of the trench itself. As mentioned in previous sections of the present disclosure, calibration procedures may be useful in establishing the lithography functionality of a large array of tips. Each of the tips may have some error in location around a planned location which may be dealt with in the calibration process. The control of the emission processing and rastering of the imaging device across the surface may be made in the circuit of the post processed e-dram device, in additional circuits with communicate with the emission device or in some examples to a degree in both onboard and outboard circuits that are interconnected.

In some examples, embedded dram processes create trenches in a 22 nm. process where the trenches may be on the order of 240 nm. in size and separation. In some examples, the resulting emission tips as discussed herein may be able to be used without rastering. In other examples, the tips may be rastered in controlled manners to perform the lithography processing.

Cell Printing

In some examples, the multiple print head devices as have been described may be used to print single cells upon a substrate. in some examples, a droplet containing a cell in a liquid media, such as growth media, may be printed. In some other examples, the cell may be printed alone. There may be numerous types of cells that may be printed at different locations determined by a model used to control the print head. The different cells may be grown from stem cell parents obtained or created from cellular material of a patient. Through various means, the stem cells may be differentiated and grown up to larger volumes of cells for printing. The multiple print heads may be fed in channels that form a row of print heads. In other examples, each print head may be positioned with its own reservoir that may contain a sample of cells for that print head alone. The print heads may be fed by reservoirs and piping and pipetting systems, or in some examples the print head may be married to a microfluidic processing element that may allow material to be distributed to any of the means of distribution to the print heads.

Stem Cells and Biochemical Processing for Differentiation

Figure 16A:
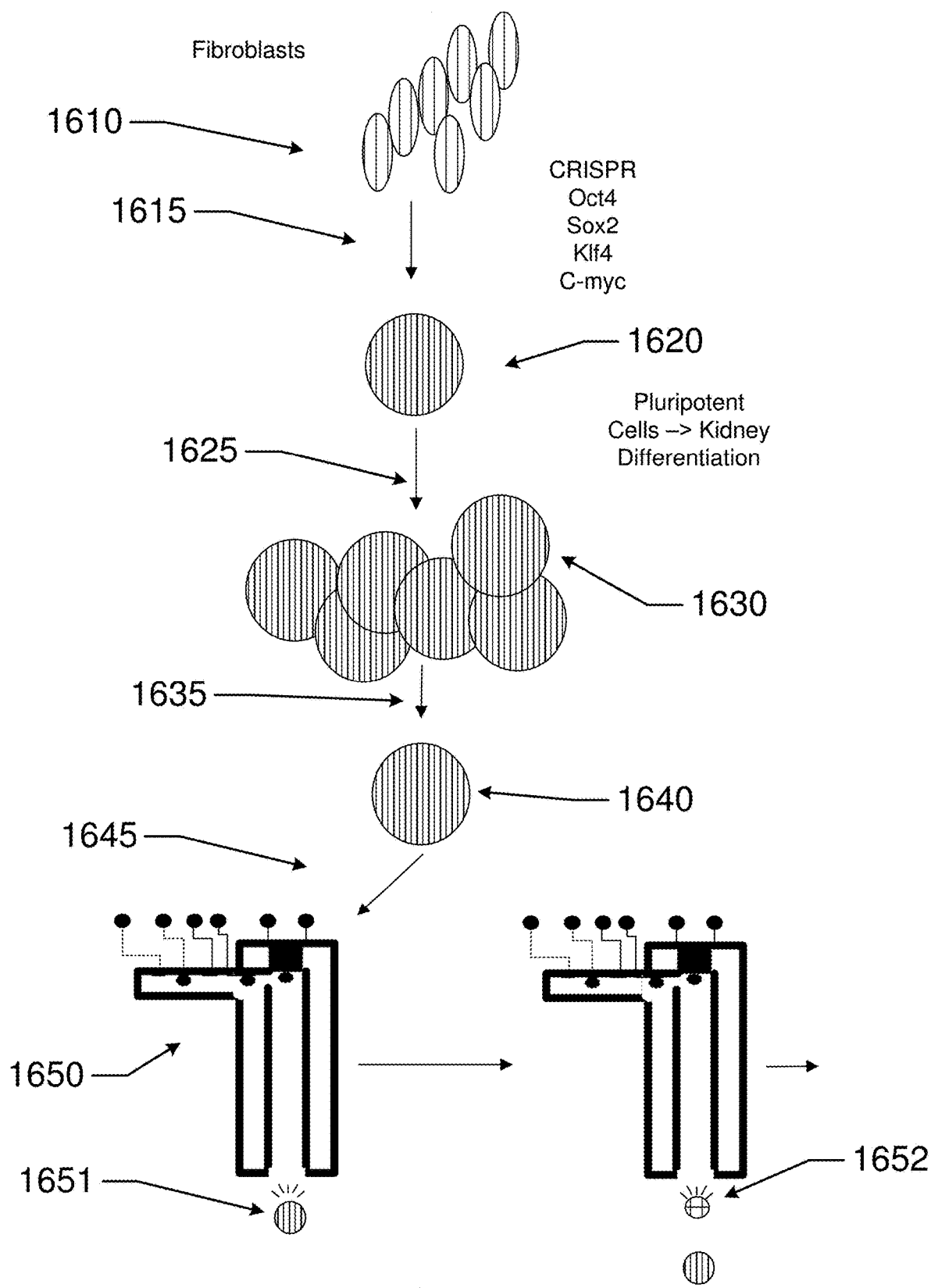
FIG. 16A—An exemplary processing flow for printing of cells.

In some examples, a large print head with many individual printing element, such as over 10,000 for example, may be used to print relatively large areas with cells of different types to form tissues with the deposition. In a non-limiting example, cells to be printed may be cells of an individual patient, where the printed cells are grown from a cell line that originates with the patient him/herself. Referring to FIG. 16A, an example of printing cells from a patient is illustrated. A sample of cells may be obtained from the patient such as the exemplary fibroblast cells 1610 which may be isolated from a sample of a patient's skin. There may be numerous manners to induce the sample cells to become stem cells which will have the potential to grow and multiply. In a non-limiting example genetic modification of the fibroblast cells may be performed. In an example, a transcription technique or gene editing technique 1615 such as those based on CRISPR-cas9 may be used to induce alteration of a series of genes such as the OCT4, SOX2, KLF4 and C-MYC genes which have been shown to induce pluripotency. The pluripotent cells 1620 may be grown up and multiplied 1625 to a collection of pluripotent kidney cells 1630. In some examples the growing collection of cells may be dissociated by physical or chemical means and separated 1635. In some examples, separation of any cells that are not pluripotent may be accorded by the binding of antibodies to the cells that differentiate the different cell types. The different cells some with bound antibodies which may have a fluorescent marker attached or may be a substrate for an additional antibody that has a fluorescent marker may be sorted based on the fluorescent signals of the antibodies or other dyes. The separated individual pluripotent cells 1640 may be loaded or passed 1645 into the printing system. A printing system of the type herein may print 1650 the cell 1651 either in a droplet of media or by itself at a location that is determined by an algorithm that processes a model of the location of various cell types. In some examples, another material may be printed after the cell is printed. This additional material may include the addition of recombinant growth factors or small agonists 1652 that may guide the pluripotent stem cell to differentiate into a desired type of cell for the location.

Figure 16B:
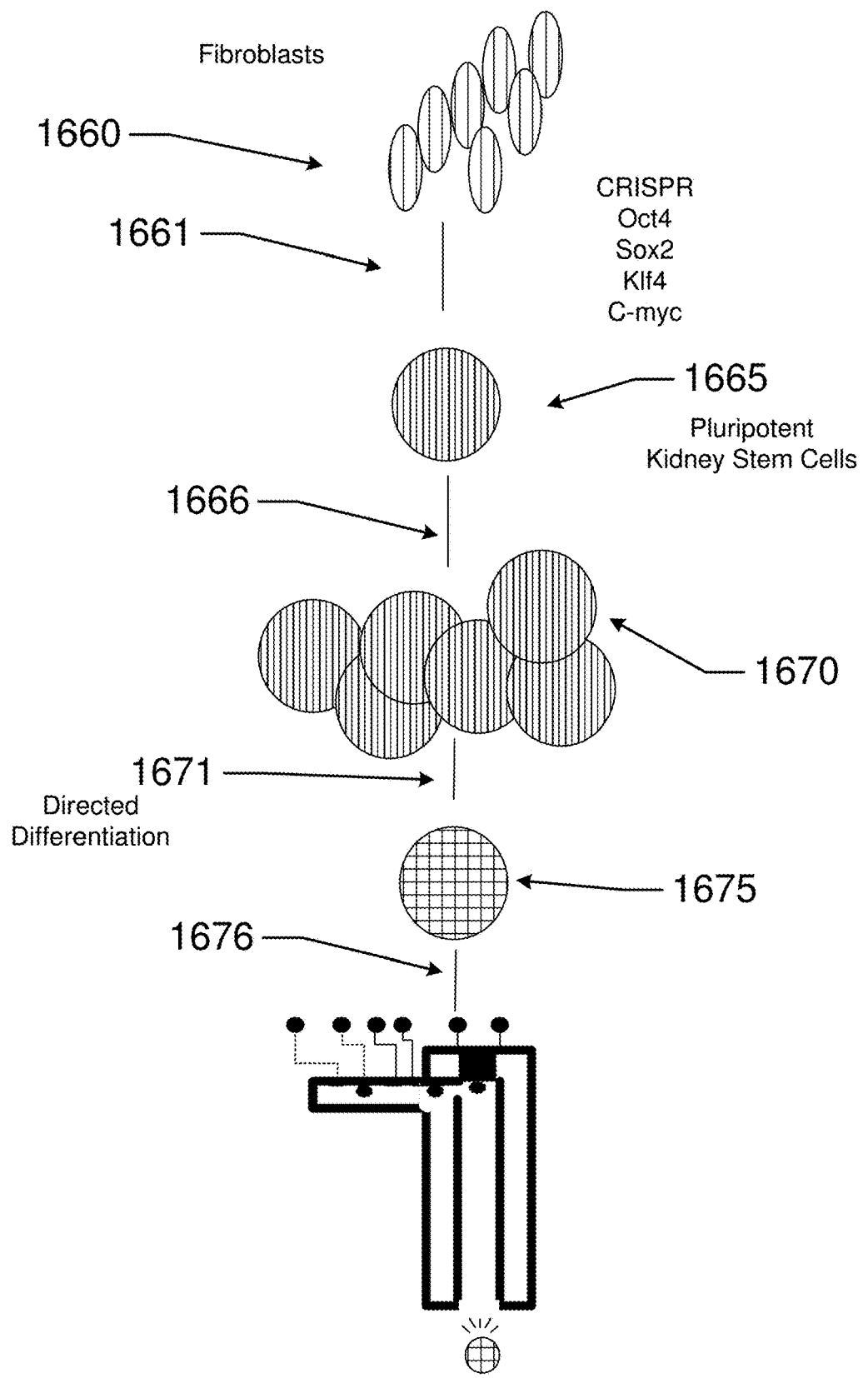
FIG. 16B—An alternative exemplary processing flow for the printing of cells.
Figure 17:
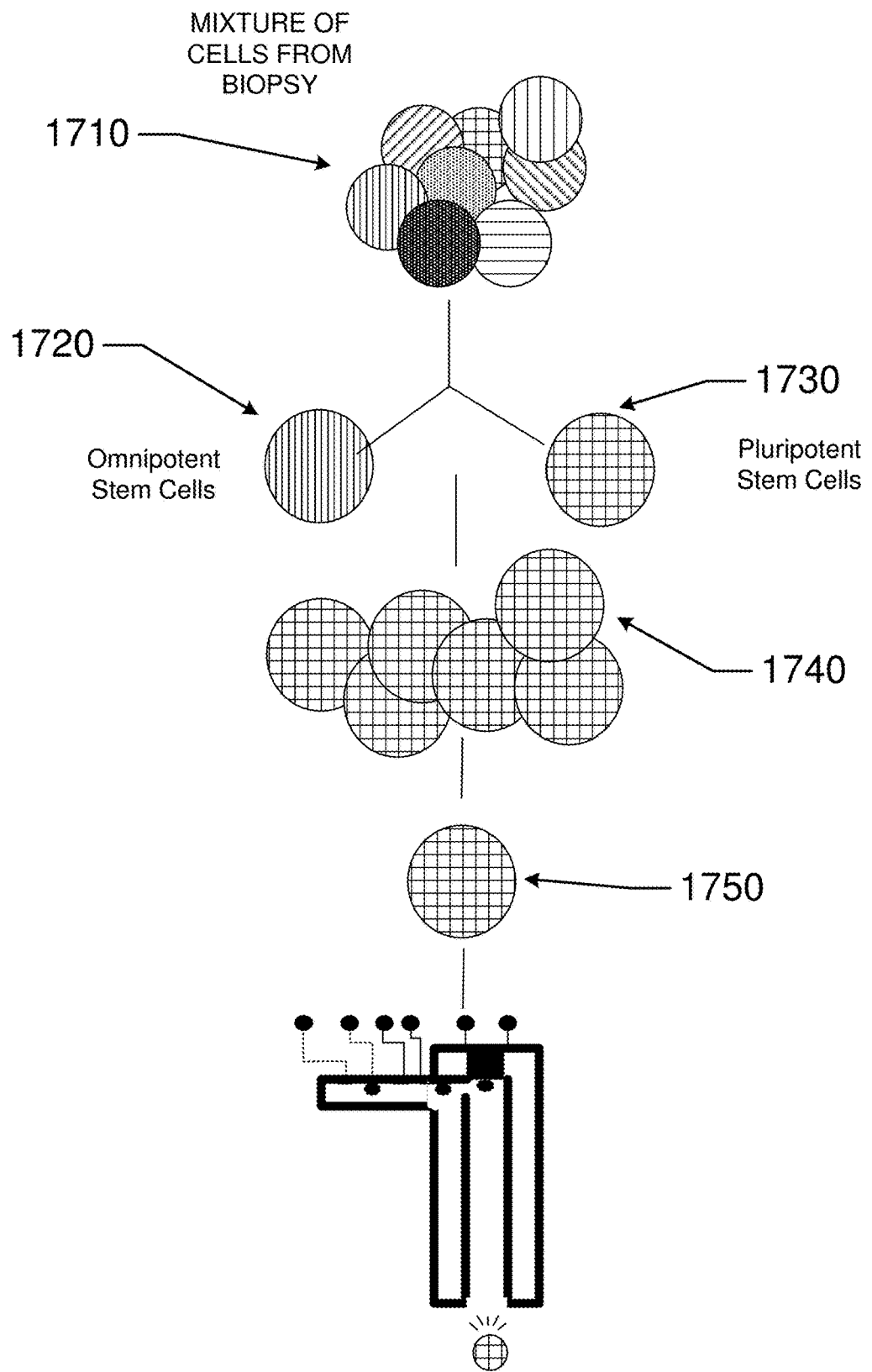
FIG. 17—An alternative exemplary processing flow for the printing of cells.

Referring to FIG. 16B, a different printing scheme may be observed. A sample of cells may be obtained from the patient such as the exemplary fibroblast cells 1660 which may be isolated from a sample of a patient's skin. There may be numerous manners to induce the sample cells to become stem cells which will have the potential to grow and multiply. In a non-limiting example genetic modification of the fibroblast cells may be performed. In an example, a transcription technique or gene editing technique 1661 such as those based on CRISPR-cas9 may be used to induce alteration of a series of genes such as the OCT4, SOX2, KLF4 and C-MYC genes which have been shown to induce pluripotency. The pluripotent cells 1665 may be grown up 1666 to a collection 1670 and influenced with the addition of recombinant growth factors or small agonists 1671 to differentiate into various Kidney cell types 1675. In some examples, the Kidney type differentiated cells can form embryonic forms of key Kidney elements including the nephron and early stage elements including the glomerulus and the uterine system. In some examples the growing elements may be dissociated by physical or chemical means and separated. In some examples, separation may be accorded by the binding of antibodies to the cells that differentiate the different cell types and may be sorted based on the fluorescent signals of the antibodies or other dyes. Other separation schemes may be employed. The separated individual cell types 1675 may be loaded or passed 1676 into the printing system. A printing system of the type herein may print the cell either in a droplet of media or by itself at a location that is determined by an algorithm that processes a model of the location of various cell types. In some examples, another material may be printed after the cell is printed Other organ types or tissue types may be processed in analogous means. The examples relating to kidney cells are just one of many examples which may include skin, bone, heart, liver, colon, thyroid, brain, muscle and other types. Referring to FIG. 17 an alternative method of printing cells is illustrated. A mixture of cells may be collected from a biopsy 1710 of a patient. In some examples, the biopsy may include a small number of stem type cells. In some examples, which may be very rare, omnipotent stem cells 1720 may be found. Such cells could be used for printing schemes. In other examples, pluripotent stem cells may be located within portions of an associated organ, such as kidney pluripotent stem cells 1730. These pluripotent stem cells 1730 may be grown up and multiplied 1740. In some examples the growing collection of cells may be dissociated by physical or chemical means and separated. In some examples, separation of any cells that are not pluripotent may be accorded by the binding of antibodies to the cells that differentiate the different cell types. The different cells some with bound antibodies which may have a fluorescent marker attached or may be a substrate for an additional antibody that has a fluorescent marker may be sorted based on the fluorescent signals of the antibodies or other dyes. The separated individual pluripotent cells 1750 may be loaded or passed into the printing system. A printing system of the type herein may print the cell either in a droplet of media or by itself at a location that is determined by an algorithm that processes a model of the location of various cell types. In some examples, another material may be printed after the cell is printed. This additional material may include the addition of recombinant growth factors or small agonists that may guide the pluripotent stem cell to differentiate into a desired type of cell for the location.

Exemplary Microfluidic Processing System with Chemical Imaging System

Figure 18:
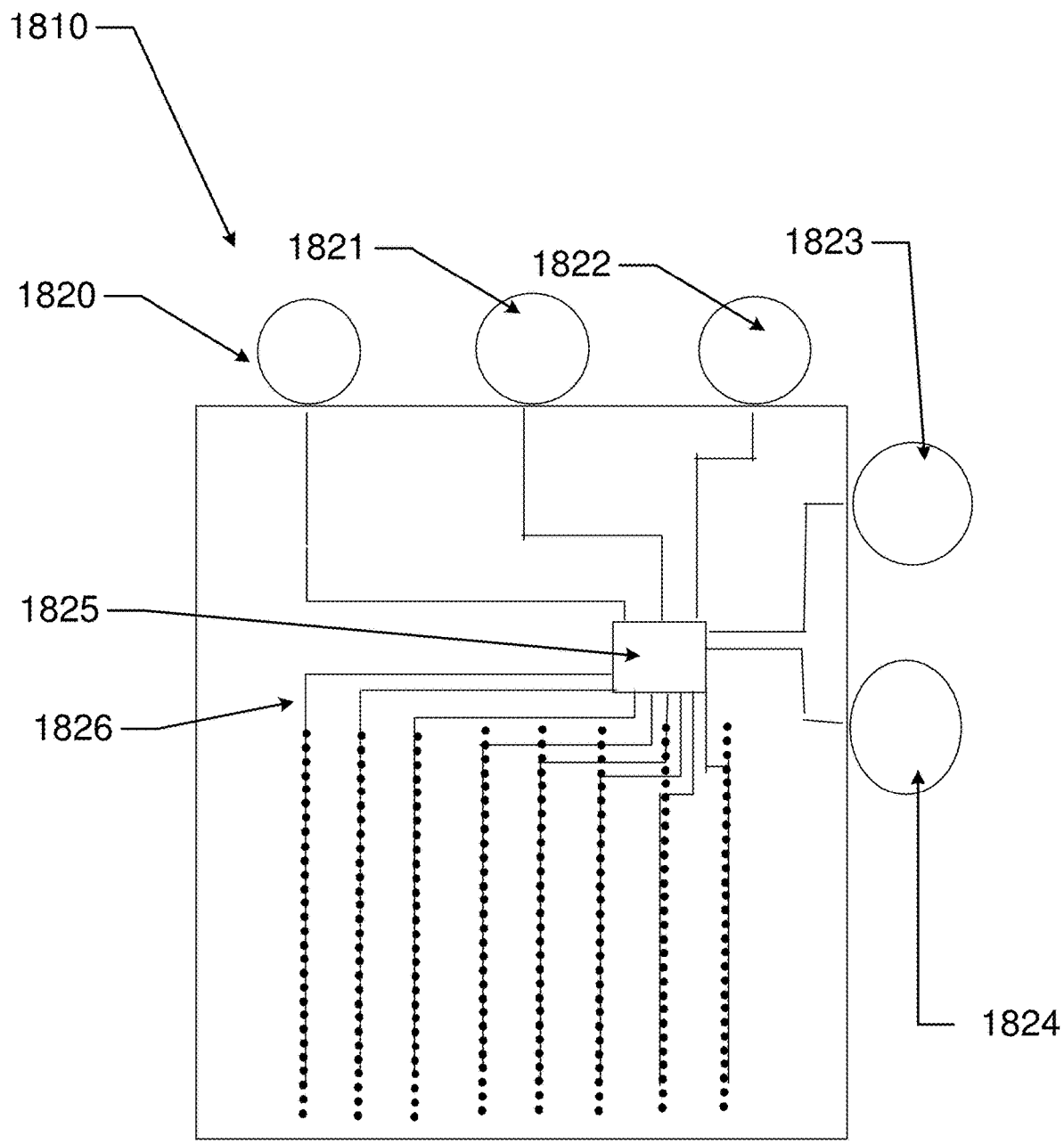
FIG. 18—An exemplary printing device with attached microfluidic processor.

Referring to FIG. 18 a combination of a microfluidic processing system 1810 with a multi-printing head imaging system may be formed to process cells in the various manners that have been described. In some examples a collection of differentiated cell types may be placed in reservoirs of a microfluid system. In other examples a single collection of pluripotent stem cells may be located in reservoir 1820. Different recombinant growth factors or small agonists may be located in other reservoirs 1821 and 1822 for example. Other reservoirs may contain antibodies for the identification of the pluripotent stem cells 1823 and 1824. A central processing region 1825 of the microfluidic system may combine the cells with reagents. Fluorescent techniques may be used to perform sorting actions within the microfluidic processor. In addition reagents may be mixed with cells. The resulting cell containing droplets may be individually passed to different printing elements with dedicated channels such as the example printing channel 1826 which may supply a row of printing elements. In other example each printing element may have a dedicated supply channel. In some examples, the supply channel may provide droplets down a level to a printing imaging level located beneath the microfluidic processing cell. In other examples, the microfluidic processing unit may be located in a peripheral location to the printing apparatus on the same or similarly located plane.

Printing Tissue Films with Multiple Cell Types with Chemical Imaging System

Figure 19A:
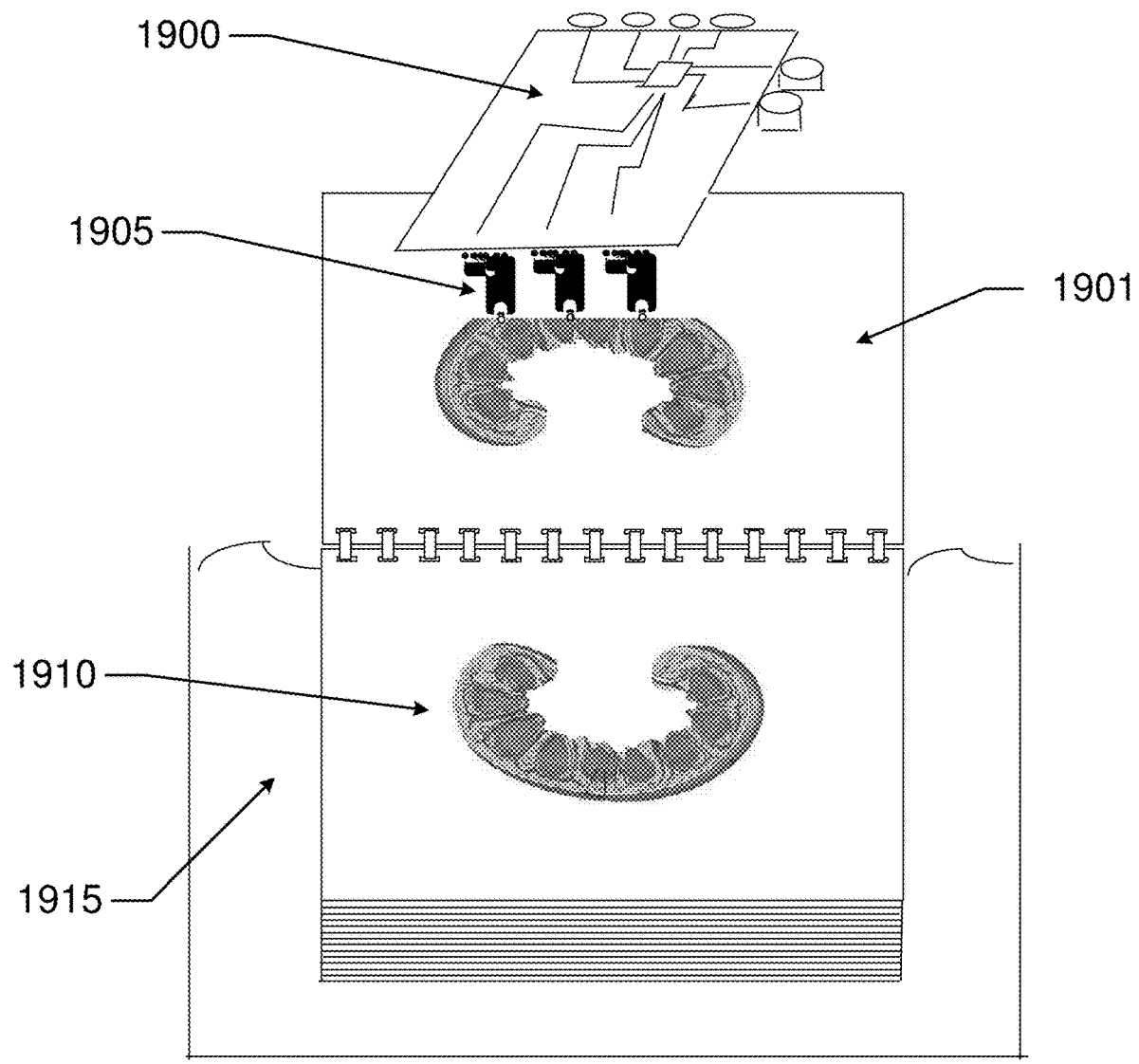
FIGS. 19A-D—An exemplary processing flow for the production of a kidney organ.

Referring to FIG. 19A, a method to print tissue layers using the concepts discussed herein is illustrated. A microfluidic processor with attached printing array element 1900 is illustrated processing a flat substrate 1901 to print 1905 on tissue layers. The substrate may be formed of a variety of materials. In some examples, the substrate may be formed of biomaterials such as collagen or collagen related materials. In other examples reabsorbable materials from synthetic materials may be used. In some examples, the substrate may be processed to remove regions of the body of the sheet. Onto the substrate, cells may be printed resulting in a tissue layer 1910 that may be stored in a nourishing medium 1915. The cells may grow from the locations that they were printed in. Depending on the resolution of the printing system, small features may not be able to be imaged by the printing means.

Figure 19B:
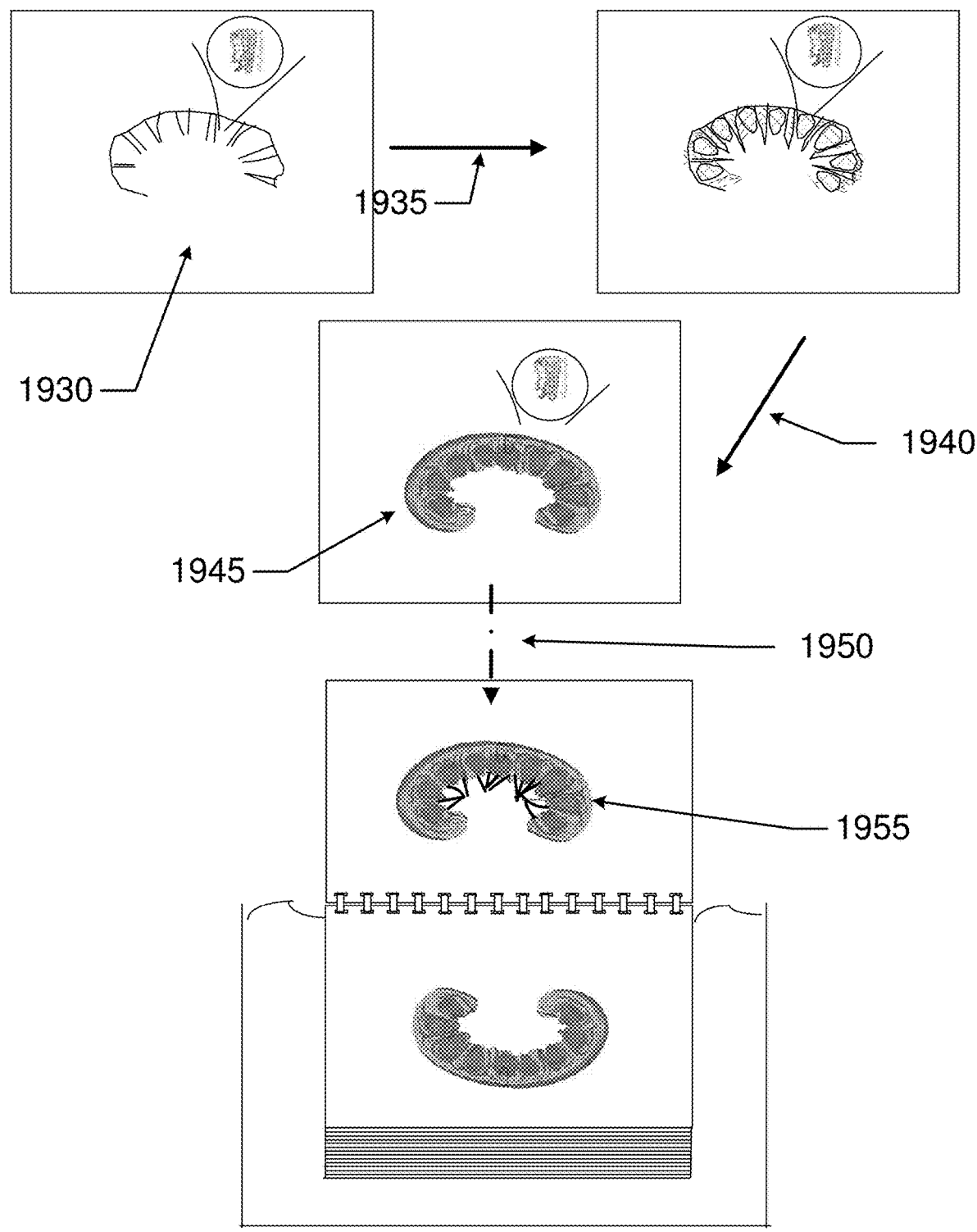
Figure 19C:
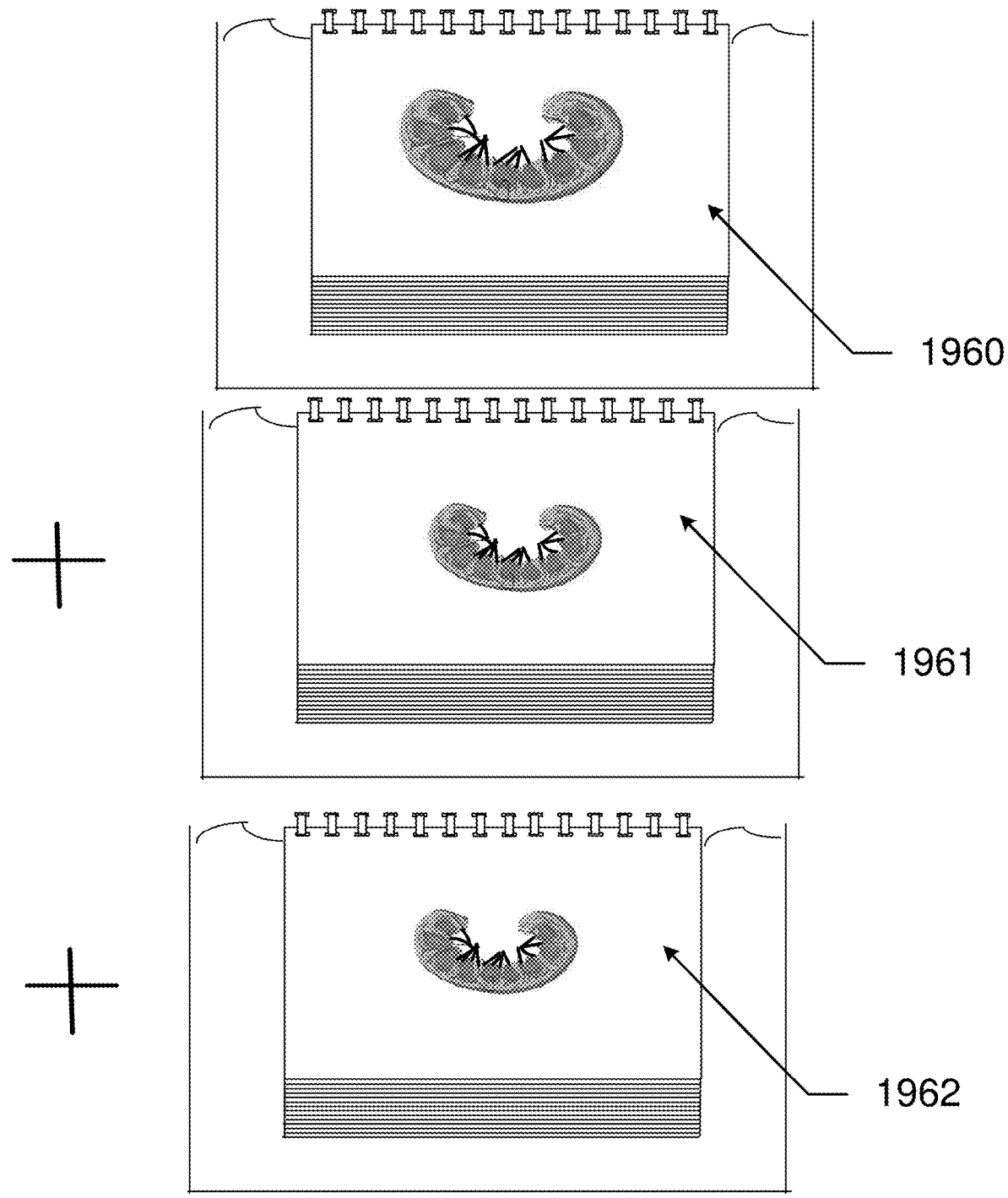
Figure 19D:
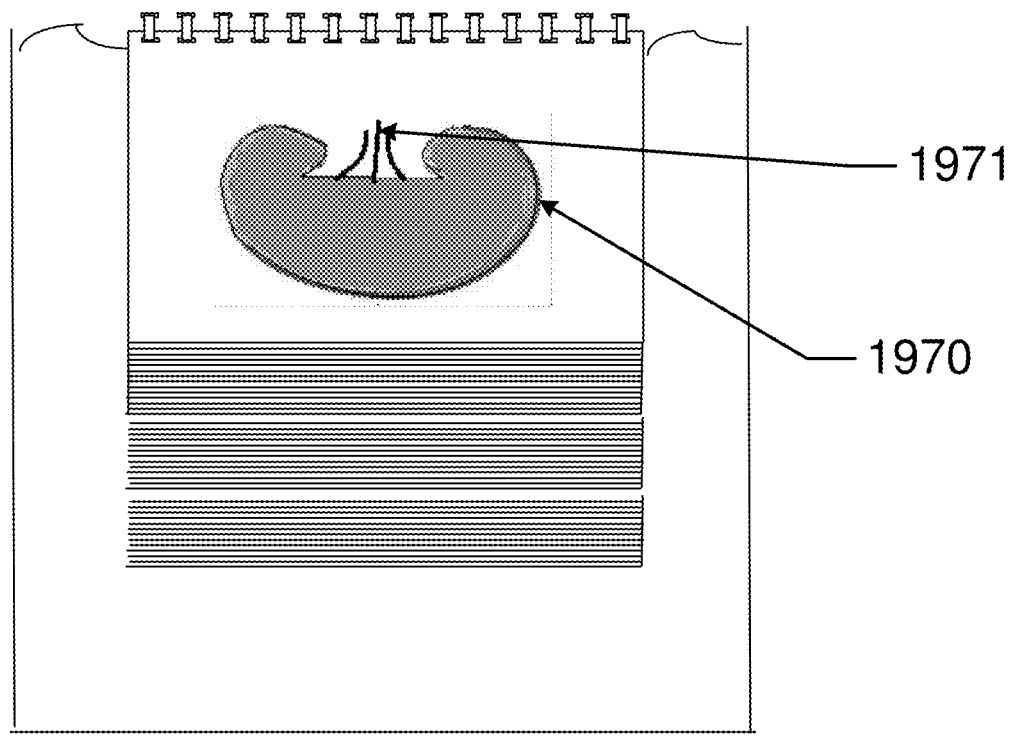

Referring to FIG. 19B, another processing means such as techniques used in microelectronics processing may be used to form matrixes with small form factors. Techniques such as film deposition, resist deposition, reactive ion etching, chemical etching, and other such techniques may be used to form small structures 1930. In an example of a kidney production, structure such as the nephron, glomerulus, uteric body and the like may have small structure used to create collections of cells that may grow into the small structures. Various means may be used to deposit cells of appropriate types upon the small support structures 1935. The support structures may have molecules absorbed to them that attract certain types of cells to bind at appropriate regions. In other examples, layers of cells may be applied or printed in sequential processing to form small structures with differentiated cells in various locations. The sheets of material with the small structures may be applied 1940 upon the other printed structures. A number of substrates with small structures 1945 may be applied upon the previously printed tissue. In some examples, additional printing steps 1950 may be used to print cells that may form vascular structure into appropriate regions of the growing layer which may interattach other formed structures 1955. Collections of layers processed in the above manners, perhaps dozens or hundreds of such layers may be stacked upon each other and then allowed to grow. Referring to FIG. 19C three layers 1960, 1961 and 1962 may be stacked upon each other. Referring to FIG. 19D, the multiple stacked layers 1970 may grow into a formed organ. In some examples additional structures such as the renal veins and arteries as well as ureter structures may be attached 1971.

Measurements of Imaged and Grown Tissues

The assembled tissue layers may be surrounded in growth media in some examples which can provide energy containing constituents, gasses and other important nutritive compounds that the cells can ingest. The environment may support the cells and layers of cells to grow together into integrated tissues and organs. In some examples the forming of the layers before assembly may include printing of cells and regional placement of signaling molecules that can induce changes and differentiated characteristics to the cells. The changes may manifest as changes at many different levels ranging from changes in expression of proteins, in the expression of transcriptomes, in expression of epigenomes, or in changes to the genome itself. These changes may be important to the end function of the three dimensionally located cells and may impart correct function to the resulting tissues and organs that may be imaged and grown.

In some examples, the growing tissue structure may be monitored by various measurement techniques. As a non-limiting example of techniques that may be employed including the algorithmic processing related to such assessment, reference is made to the U.S. patent application Ser. No. 16/215,723 filed on Dec. 11, 2018 the contents of which are incorporated herein by reference. In some examples, in situ non destructive measurements of physical and chemical parameters such as pH, dissolved gas concentrations, temperature and the like may be used to monitor growth. In other examples, samples of cells from the growing tissue may be obtained and studied utilizing multi omics to characterize the nature of the changes in protein expression with proteomic measurements, in transcriptomes with transcriptomic measurement, in epigenomes with epigenomic measurements and in genetics with genomic measurements. The characterizations may result in changes to the conditions of the growth media or other processing conditions to influence the cells. In some cases, the measurements may be used to select or reject layers of cells or integrated layer products.

Glossary of Selected Terms

Reference may have been made to different aspects of some preferred embodiments of the invention, examples of which are illustrated in the accompanying drawings. A Glossary of Selected Terms is included now at the end of this Detailed Description.

Air receiving wall: a boundary wall of a cleanspace that receives air flow from the cleanspace.

Air source wall: a boundary wall of a cleanspace that is a source of clean airflow into the cleanspace.

Annular: The space defined by the bounding of an area between two closed shapes one of which is internal to the other.

Automation: The techniques and equipment used to achieve automatic operation, control or transportation.

Ballroom: A large open cleanroom space devoid in large part of support beams and walls wherein tools, equipment, operators and production materials reside.

Batches: A collection of multiple substrates to be handled or processed together as an entity Boundaries: A border or limit between two distinct spaces—in most cases herein as between two regions with different air particulate cleanliness levels.

Circular: A shape that is or nearly approximates a circle.

Clean: A state of being free from dirt, stain, or impurities—in most cases herein referring to the state of low airborne levels of particulate matter and gaseous forms of contamination.

Cleanspace (or equivalently Clean Space): A volume of air, separated by boundaries from ambient air spaces, that is clean.

Cleanspace, Primary: A cleanspace whose function, perhaps among other functions, is the transport of jobs between tools.

Cleanspace, Secondary: A cleanspace in which jobs are not transported but which exists for other functions, for example as where tool bodies may be located.

Cleanroom: A cleanspace where the boundaries are formed into the typical aspects of a room, with walls, a ceiling and a floor.

Conductive Connection: a joining of two entities which are capable of conducting electrical current with the resulting characteristics of metallic or semiconductive or relatively low resistivity materials.

Conductive Contact: a location on an electrical device or package having the function of providing a Conductive Surface to which a Conductive Connection may be made with another device, wire or electrically conductive entity.

Conductive Surface: a surface region capable of forming a conductive connection through which electrical current flow may occur consistent with the nature of a conductive connection.

Core: A segmented region of a standard cleanroom that is maintained at a different clean level. A typical use of a core is for locating the processing tools.

Ducting: Enclosed passages or channels for conveying a substance, especially a liquid or gas—typically herein for the conveyance of air.

Envelope: An enclosing structure typically forming an outer boundary of a cleanspace.

Fab (or fabricator): An entity made up of tools, facilities and a cleanspace that is used to process substrates.

Fit up: The process of installing into a new clean room the processing tools and automation it is designed to contain.

Flange: A protruding rim, edge, rib, or collar, used to strengthen an object, hold it in place, or attach it to another object. Typically as utilized herein, a Flange may also be used to seal the region around the attachment.

Folding: A process of adding or changing curvature.

HEPA: An acronym standing for high-efficiency particulate air. Used to define the type of filtration systems used to clean air.

Horizontal: A direction that is, or is close to being, perpendicular to the direction of gravitational force.

Job: A collection of substrates or a single substrate that is identified as a processing unit in a fab. This unit being relevant to transportation from one processing tool to another.

Logistics: A name for the general steps involved in transporting a job from one processing step to the next. Logistics can also encompass defining the correct tooling to perform a processing step and the scheduling of a processing step.

Maintenance Process: A series of steps that constitute the repair or retrofit of a tool or a toolPod. The steps may include aspects of disassembly, assembly, calibration, component replacement or repair, component inter-alignment, or other such actions which restore, improve or insure the continued operation of a tool or a toolPod Multifaced: A shape having multiple faces or edges.

Nonsegmented Space: A space enclosed within a continuous external boundary, where any point on the external boundary can be connected by a straight line to any other point on the external boundary and such connecting line would not need to cross the external boundary defining the space.

Perforated: Having holes or penetrations through a surface region. Herein, said penetrations allowing air to flow through the surface.

Peripheral: Of, or relating to, a periphery.

Periphery: With respect to a cleanspace, refers to a location that is on or near a boundary wall of such cleanspace. A tool located at the periphery of a primary cleanspace can have its body at any one of the following three positions relative to a boundary wall of the primary cleanspace: (i) all of the body can be located on the side of the boundary wall that is outside the primary cleanspace, (ii) the tool body can intersect the boundary wall or (iii) all of the tool body can be located on the side of the boundary wall that is inside the primary cleanspace. For all three of these positions, the tool's port is inside the primary cleanspace. For positions (i) or (iii), the tool body is adjacent to, or near, the boundary wall, with nearness being a term relative to the overall dimensions of the primary cleanspace.

Planar: Having a shape approximating the characteristics of a plane.

Plane: A surface containing all the straight lines that connect any two points on it.

Polygonal: Having the shape of a closed figure bounded by three or more line segments Process: A series of operations performed in the making or treatment of a product—herein primarily on the performing of said operations on substrates.

Processing Chamber (or Chamber or Process Chamber): a region of a tool where a substrate resides or is contained within when it is receiving a process step or a portion of a process step that acts upon the substrate. Other parts of a tool may perform support, logistic or control functions to or on a processing chamber.

Process Flow: The order and nature of combination of multiple process steps that occur from one tool to at least a second tool. There may be consolidations that occur in the definition of the process steps that still constitute a process flow as for example in a single tool performing its operation on a substrate there may be numerous steps that occur on the substrate. In some cases these numerous steps may be called process steps in other cases the combination of all the steps in a single tool that occur in one single ordered flow may be considered a single process. In the second case, a flow that moves from a process in a first tool to a process in a second tool may be a two step process flow.

Production unit: An element of a process that is acted on by processing tools to produce products. In some cleanspace fabricators this may include carriers and/or substrates.

Robot: A machine or device that operates automatically or by remote control, whose function is typically to perform the operations that move a job between tools, or that handle substrates within a tool.

Round: Any closed shape of continuous curvature.

Substrates: A body or base layer, forming a product, that supports itself and the result of processes performed on it.

Tool: A manufacturing entity designed to perform a processing step or multiple different processing steps. A tool can have the capability of interfacing with automation for handling jobs of substrates. A tool can also have single or multiple integrated chambers or processing regions. A tool can interface to facilities support as necessary and can incorporate the necessary systems for controlling its processes.

Tool Body: That portion of a tool other than the portion forming its port.

Tool Chassis (or Chassis): An entity of equipment whose prime function is to mate, connect and/or interact with a toolPod. The interaction may include the supply of various utilities to the toolPod, the communication of various types of signals, the provision of power sources. In some embodiments a Tool Chassis may support, mate or interact with an intermediate piece of equipment such as a pumping system which may then mate, support, connect or interact with a toolPod. A prime function of a Tool Chassis may be to support easy removal and replacement of toolPods and/or intermediate equipment with toolPods.

toolPod (or tool Pod or Tool Pod or similar variants): A form of a tool wherein the tool exists within a container that may be easily handled. The toolPod may have both a Tool Body and also an attached Tool Port and the Tool Port may be attached outside the container or be contiguous to the tool container. The container may contain a small clean space region for the tool body and internal components of a tool Port. The toolPod may contain the necessary infrastructure to mate, connect and interact with a Tool Chassis. The toolPod may be easily transported for reversible removal from interaction with a primary clean space environment.

Tool Port: That portion of a tool forming a point of exit or entry for jobs to be processed by the tool. Thus the port provides an interface to any job-handling automation of the tool.

Tubular: Having a shape that can be described as any closed figure projected along its perpendicular and hollowed out to some extent;

Unidirectional: Describing a flow which has a tendency to proceed generally along a particular direction albeit not exclusively in a straight path. In clean airflow, the unidirectional characteristic is important to ensuring particulate matter is moved out of the cleanspace.

Unobstructed removability: refers to geometric properties, of fabs constructed in accordance with the present invention that provide for a relatively unobstructed path by which a tool can be removed or installed.

Utilities: A broad term covering the entities created or used to support fabrication environments or their tooling, but not the processing tooling or processing space itself. This includes electricity, gasses, airflows, chemicals (and other bulk materials) and environmental controls (e.g., temperature).

Vertical: A direction that is, or is close to being, parallel to the direction of gravitational force.

Vertically Deployed Cleanspace: a cleanspace whose major dimensions of span may fit into a plane or a bended plane whose normal has a component in a horizontal direction. A Vertically Deployed Cleanspace may have a cleanspace airflow with a major component in a horizontal direction. A Ballroom Cleanroom would typically not have the characteristics of a vertically deployed cleanspace.

While the invention has been described in conjunction with specific embodiments, it is evident that many alternatives, modifications and variations will be apparent to those skilled in the art in light of the foregoing description. Accordingly, this description is intended to embrace all such alternatives, modifications and variations as fall within its spirit and scope.

What is claimed is:

1. An imaging apparatus comprising:
an array of chemical emitters, wherein the chemical emitters comprise electroactive devices on a base layer, a microfluidic chemical processor which feeds material to the chemical emitters, and wherein there are more than 2 chemical emitters in the array;
wherein the imaging apparatus is operated in a cleanspace fabricator wherein the product of the emission of the chemicals is moved within a sterile environment of the cleanspace fabricator; and
electrical circuits connected to each of the chemical emitters, wherein the electrical circuits bias the electroactive devices based on data related to a model of a tissue to be formed.

2. The imaging apparatus of claim 1 wherein the chemical emitters emit droplets which comprise living cells.

3. The imaging apparatus of claim 2 wherein the cells are omnipotent stem cells.

4. The imaging apparatus of claim 2 wherein the number of chemical emitters exceeds 10.

5. The imaging apparatus of claim 4 wherein the chemical emitters emit droplets that are about 50 microns in size.

* * * * *